United States Patent
Lee et al.

(10) Patent No.: US 7,629,119 B2
(45) Date of Patent: Dec. 8, 2009

(54) ANIMAL GENOTYPING METHOD

(75) Inventors: Michael Ah Lee, Dunedin (NZ); Michael Lewis Tate, Dunedin (NZ)

(73) Assignee: A2 Corporation Limited, Dunedin (NZ)

( * ) Notice: Subject to any disclaimer, the term of this patent is extended or adjusted under 35 U.S.C. 154(b) by 647 days.

(21) Appl. No.: 10/515,940

(22) PCT Filed: May 23, 2003

(86) PCT No.: PCT/NZ03/00102

§ 371 (c)(1),
(2), (4) Date: Sep. 9, 2005

(87) PCT Pub. No.: WO03/100074

PCT Pub. Date: Dec. 4, 2003

(65) Prior Publication Data

US 2007/0264408 A1    Nov. 15, 2007

(30) Foreign Application Priority Data

May 24, 2002  (NZ) .................................... 519166

(51) Int. Cl.
*C12Q 1/68*    (2006.01)
(52) U.S. Cl. ........................................................ 435/6
(58) Field of Classification Search ................... None
See application file for complete search history.

(56) References Cited

U.S. PATENT DOCUMENTS 6,222,094 B1 * 4/2001 Hansson et al. ............... 800/14
6,570,060 B2 * 5/2003 McLachlan .................... 800/8

FOREIGN PATENT DOCUMENTS

WO         96/14577        5/1996
WO    WO-96-36239 A1  * 11/1996

OTHER PUBLICATIONS

Martin et al., "The impact of genetic polymorphisms on the protein composition of ruminant milks", Reprod. Nutr. Dev. 42, 2002, pp. 433-459.
Groves et al., "Composition of Bovine γ-Caseins $A^1$ and $A^3$, and Further Evidence For a Relationship in Biosynthesis of γ- and β-Caseins", J Dairy Sci, vol. 55, No. 8, 1972, pp. 1041-1049.
Hines et al., "Linkage Relationships Among Loci of Polymorphisms in Blood and Milk of Cattle[1,2,3,4]", J Dairy Sci, Vo. 64, No. 1, 1981, pp. 71-76.
Threadgill et al., "Genomic analysis of the major bovine milk protein genes", Nucleic Acids Research, vol. 18, No. 23, pp. 6935-6942.
K.F. Ng-Kwai-Hang, "A review of the relationship between milk protein polymorphism and milk composition/milk production", International Dairy Federation [Special Issue] S.I., 1997, pp. 23-37.
AS Truswell, "Review—The A2 milk case: a critical review", European Journal of Clinical Nutrition (2005), 59, pp. 623-631.
Lien S et al.: "A Simple and Powerful Method for Linkage Analysis by Amplification of DNA from Single Sperm Cells" Genomics, Academic Press, San Diego, US vol. 16, No. 1, dated Apr. 1, 1993 pp. 41-44, XP024797158.
Groenen M A M et al. "The complete sequence of the gene encoding bovine alpha2-casein" Gene, Elsevier, Amsterdam, NL vol. 123, No. 2, Jan. 30, 1993, p. 187-193, XP023183961.
Martin p et al.: "The impact of genetic polymorphisms on the protein composition of ruminant milks" Sep. 1, 2002, Reproduction, Nutrition, Development, Paris, FR, pp. 433-459, XP008088224.
European Patent Office issued a Supplementary European Search Report dated Jan. 16, 2009, Application No. 03 72 8181.

* cited by examiner

*Primary Examiner*—James Martinell
(74) *Attorney, Agent, or Firm*—Young & Thompson

(57) ABSTRACT

This invention relates to a method for determining whether a bovine animal possesses a gene for β-casein $A^2$ or the gene for β-casein $A^1$ in its milk by testing the DNA of the bovine animal for the presence of at least one DNA marker (excluding those DNA markers present in the sequence of the genes themselves). In particular, the method uses SNPs as DNA markers for the β-casein $A^2$ and β-casein $A^1$ genes.

15 Claims, 15 Drawing Sheets

FIGURE 1 illegible sequence alignment figure with SEQ ID NO: 31 through SEQ ID NO: 40 and SEQ ID NO: 51

FIGURE 1 CONTINUED

```
P6-82_t3   > TATGTTGTCACAAACTTGATTTGCTTTGTCATATCA.TTTTTTCCCTCCATATGATGAAA
169
P5-82_t3   > TATGTTGTCACAAACTTGATTTGCTTTGTCATATCA.TTTTTTCCCTCCATATGATGAAA
169
P7-82_t3   > TATGTTGTCACAAACTTGATTTGCTTTGTCATATCA.TTTTTTCCCTCCATATGATGAAA
174
P9-82_t3   > TATGTTGTCACAAACTTGATTTGCTTTGTCATATCATTTTTTTCCCTCCATATGATGAAA
177
P1-82_t3   > TATGTTGTCACAAACTTGATTTGCTTTGTCATATCA.TTTTTTCCCTCCATATGATGAAA
177
P8-82_t3   > TATGTTGTCACAAACTTGATTTGCTTTGTCATATCA.TTTTTTCCCTCCATATGATGAAA
180
P10-82_t3  > TATGTTGTCACAAACTTGATTTGCTTTGTCATATCA.TTTTTTCCCTCCATATGATGAAA
180
P4-82_t3   > TATGTTGTCACAAACTTGATTTGCTTTGTCATATCA.TTTTTTCCCTCCATATGATGAAA
180
P3-82_t3   > TATGTTGTCACAAACTTGATTTGCTTTGTCATATCA.TTTTTTCCCTCCATATGATGAAA
180
P2-82_t3   > TATGTTGTCACAAACTTGATTTGCTTTGTCATATCA.TTTTTTCCCTCCATATGATGAAA
180
CONSENSUS  > TATGTTGTCACAAACTTGATTTGCTTTGTCATATCA.TTTTTTCCCTCCATATGATGAAA
180
             .........+.........+.........+.........+.........+.........+

P6-82_t3   > AGGATCAGACTACTTCGCAAAATAATTTTCTGTGAAAAAAA.AGAATAACCATTATGAGT
229
P5-82_t3   > AGGATCAGACTACTTCGCAAAATAATTTTCTGTGAAAAAAGAGAATAACCATTATGAGT
229
P7-82_t3   > AGGATCAGACTACTTCGCGAAATAATTTTCTGTGAAAAAAA.AGAATAACCATTATGAGT
234
P9-82_t3   > AGGATCAGACTACTTCGCAAAATAATTTTCTGTGAAAAAAA.AGAATAACCATTATGAGT
237
P1-82_t3   > AGGATCAGACTACTTCGCAAAATAATTTTCTGTGAAAAAAA.AGAATAACCATTATGAGT
237
P8-82_t3   > AGGATCAGACTACTTCGCAAAATAATTTTCTGTGAAAAAAA.AGAATAACCATTATGAGT
240
P10-82_t3  > AGGATCAGACTACTTCGCAAAATAATTTTCTGTGAAAAAAA.AGAATAACCATTATGAGT
240
P4-82_t3   > AGGATCAGACTACTTCGCAAAATAATTTTCTGTGAAAAAAA.AGAATAACCATTATGAGT
240
P3-82_t3   > AGGATCAGACTACTTCGCAGAATAATTTTCTGTGAAAAAAA.AGAATAACCATTATGAGT
240
P2-82_t3   > AGGATCAGACTACTTCGCAAAATAATTTTCTGTGAAAAAAA.AGAATAACCATTATGAGT
240
CONSENSUS  > AGGATCAGACTACTTCGCaAATAATTTTCTGTGAAAAAAA.AGAATAACCATTATGAGT
240
             .........+.........+.........+.........+.........+.........+

P6-82_t3   > ATGAGCTGAATATTCAGTTGTGTTTAATAAATAGCCTTTTTCACTTTGCTATCATTATTT
289
P5-82_t3   > ATGAGCTGAATATTCAGTTGTGTTTAATAAATAGCCTTTTTCACTTTGCTATCATTATTT
289
P7-82_t3   > ATGAGCTGAATATTCAGTTGTGTTTAATAAAAGCCTTTTTCACTTTGCTATCATTATTT
294
P9-82_t3   > ATGAGCTGAATATTCAGTTGTGTTTAATAAATAGCCTTTTTCACTTTGCTATCATTATTT
297
P1-82_t3   > ATGAGCTGAATATTCAGTTGTGTTTAATAAATAGCCTTTTTCACTTTGCTATCATTATTT
297
P8-82_t3   > ATGAGCTGAATATTCAGTTGTGTTTAATAAATAGCCTTTTTCACTTTGCTATCATTATTT
300
P10-82_t3  > ATGAGCTGAATATTCAGTTGTGTTTAATAAATAGCCTTTTTCACTTTGCTATCATTATTT
300
P4-82_t3   > ATGAGCTGAATATTCAGTTGTGTTTAATAAATAGCCTTTTTCACTTTGCTATCATTATTT
300
```

FIGURE 1 CONTINUED

```
           P3-82_t3    > ATGAGCTGAATATTCAGTTGTGTTTAATAAATAGCCTTTTTCACTTTGCTATCATTATTT
           300
           P2-82_t3    > ATGAGCTGAATATTCAGTTGTGTTTAATAAATAGCCTTTTTCACTTTGCTATCATTATTT
           300
           CONSENSUS   > ATGAGCTGAATATTCAGTTGTGTTTAATAAAtAGCCTTTTTCACTTTGCTATCATTATTT
           300
                        .........+.........+.........+.........+.........+.........+
SEQ ID NO:
     49    P4-82_t7    <                                                   AGAGACAGT.A
           11
     50    P2-82_t7    <                                       GTCCCATAATG.GAGAGACATG.A
           24
           P6-82_t3    > ATATACTTATTCTGCATTTAAAAACAATGATCATGTGTTCCATAATGTGAGAGACATGAA
           349
           P5-82_t3    > ATATACTTATTCTGCATTTAAAAACAATGATCATGTGTTCCATAATGTGAGAGACATGAA
           349
           P7-82_t3    > ATATACTTATTCTGCATTTAAAAACAATGATCATGTGTTCCATAATGTGAGAGACATGAA
           354
           P9-82_t3    > ATATACTTATTCTGCATTTAAAAACAATGATCATGTGTTCCATAATGTGAGAGACATGAA
           357
           P1-82_t3    > ATATACTTATTCTGCATTT.AAAACAATGATCATGTGTTCCATAATGTGAGAGACATGAA
           357
           P8-82_t3    > ATATACTTATTCTGCATTTAAAAACAATGATCATGTGTTCCATAATGTGAGAGACATGAA
           360
           P10-82_t3   > ATATACTTATTCTGCATTTAAAAACAATGATCATGTGTTCCATAATGTGAGGGACATGAA
           360
           P4-82_t3    > ATATACTTATTCTGCATTAAAAAACAATGATCATGTGTTCCATAATGTGAGAGACATGAA
           360
           P3-82_t3    > ATATACTTATTCTGCATTTAAAAACAATGATCATGTGTTCCATAATGTGAGAGACATGAA
           360
           P2-82_t3    > ATATACTTATTCTGCATTTAAAAACAATGATCATGTGTTCCATAATGTGAGAGACATGAA
           360
           CONSENSUS   > ATATACTTATTCTGCATTtaAAAACAATGATCATGTGTtCCATAATGtGAGaGACAtgaA
           360
                        .........+.........+.........+.........+.........+.........+
SEQ ID NO:
     43    P10-82_t7   <                                                          CACA
           4
     44    P8-82_t7    <                                                      AAGTCACA
           8
     45    P3-82_t7    <                                     TAAGCTCTAT.CTAGACAAAGTCACA
           26
     46    P1-82_t7    <                         AACT.ATCCTCAT.AAGCCC.ATTCCAGACAA.G.CACA
           39
     47    P7-82_t7    <                         ACCAAACTTATCCCCATTAAGCCCTATCCTAGACAAAGTCACA
           43
     48    P6-82_t7    <         AAATA...AGGTACCAAACTTATCCTCATTAAGCTCTATTCTAGACAAAGTCACA
           54
           P4-82_t7    < GGAGACAAAAAT.AGGTACCAAACTTATCCCCATTAAGCTCTATTCTAGACAAAGTCACA
           71
           P2-82_t7    < GGGGACAAAAAT.AGGTACCAAACTTACCCCCATTAAGCCCTATCCTAGACAAAGTCACA
           84
           P6-82_t3    > GGAGACAAAAATAAGGTACCAAACTTATCCTCATTAAGCTCTATTCTAGACAAAGTCACA
           409
           P5-82_t3    > GGAGACAAAAATAAGGTACCAAACTTATCCTCATTAAGCTCTATTCTAGACAAAGTCACA
           409
           P7-82_t3    > GGAGACAAAAATAAGGTACCAAACTTATCCTCATTAAGCTCTATTCTAGACAAAGTCACA
           414
           P9-82_t3    > GAAGACAAAAATAAGGTACCAAACTTATCCTCATTAAGCTCTATTCAAGACAAAGTCACA
           417
```

FIGURE 1 CONTINUED

```
P1-82_t3   > GGAGACAAAAATAAGGTACCAAACTTATCCTCATTAAGCTCTATTCTAGACAAAGTCACA
417
P8-82_t3   > GGAGACAAAAATAAGGTACCAAACTTATCCTCATTAAGCTCTATTCTAGACAAAGTCACA
420
P10-82_t3  > GGAGACAAAAATAAGGTACCAAACTTATCCTCATTAAGCTCTATTCTAGACAAAGTCACA
420
P4-82_t3   > GGAGACAAAAATAAGGTACCAAACTTATCCTCATTAAGCTCTATTCTAGACAAAGTCACA
420
P3-82_t3   > GGAGACAAAAATAAGGTACCAAACTTATCCTCATTAAGCTCTATTCTAGACAAAGTCACA
420
P2-82_t3   > GGAGACAAAAATAAGGTACCAAACTTATCCTCATTAAGCTCTATTCTAGACAAAGTCACA
420
CONSENSUS  > GgaGACAAAaAtaAGGTACCAAACTtAtCCtCATtAAGCtCtATtCtAGACAaGtCACA
420
```

SEQ ID NO:       .........+.........+.........+.........+.........+.........+

```
42 P5-82_t7   <    ATGCAATACAAGGTACCAGATGCTAAGT.AGAGACATCAGAAATATGGGGTAGTACA
57
P10-82_t7  < GTAATGCAAAACAAGGTACCAGATGCTAAGTTAGAGACACCAGAAATATG.GGGAGTACA
64
P8-82_t7   < GTAATGCAATACA.GGTACCAGATGCTAAGTTAGAGACATCAGAAATATGTGGTAGTACA
68
P3-82_t7   < GAA.TGCAAAACAAGG.ACCAGATGCTAAGTTAGAGACATCAGAAATATGTGGTAGTACA
86
P1-82_t7   < GAA.TGCAA.ACAAG.TACCAG.TGCTAAGTT.G.GTCATCAGAA.TATG.GGTAGTACA
99
P7-82_t7   < GAAATGCAGTACAAGGTACCAGATGCTTAGTTAGAGACATCAGAAATATGTGGTAGTACA
103
P6-82_t7   < GAAATGCAATACAAGGTACCAGATGCTAAGTTAGAGACATCAGAAATATGTGGTAGTACA
114
P4-82_t7   < GAAATGCAATACATGGTACCAGATGCTTAGTTAGAGACATCAGAAATATGTGGTAGTACA
131
P2-82_t7   < GAAATGCAATACAAGGTACCAGATGCTAAGTTAGAGACATCAGAAATATGTGGTAGTACA
144
P6-82_t3   > GAAATGCAATACAAGGTACCAGATGCTAAGTTAGAGACATCAGAAATATGTGGTAGTACA
469
P5-82_t3   > GAAATGCAATACAAGGTACCAGATGCTAAGTTAGAGACATCAGAAATATGTGGTAGTACA
469
P7-82_t3   > GAAATGCAGTACAAGGTACCAGATGCTAAGTTAGAGACATCAGAAATATGTGGTAGTACA
474
P9-82_t3   > GAAATGCAATACAAGGTACCAGATGCTAAGTTAGAGACATCAGAAATATGTGGTAGTACA
477
P1-82_t3   > GAAATGCAATACAAGGTACCAGATGCTAAGTTAGAGACATCAGAAATATGTGGTAGTACA
477
P8-82_t3   > GAAATGCAATACAAGGTACCAGATGCTAAGTTAGAGACATCAGAAATATGTGGTAGTACA
480
P10-82_t3  > GAAATGCAATACAAGGTACCAGATGCTAAGTTAGAGACATCAGAAATATGTGGTAGTACA
480
P4-82_t3   > GAAATGCAATACAAGGTACCAGATGCTAAGTTAGAGACATCAGAAATATGTGGTAGTACA
480
P3-82_t3   > GAAATGCAATACAAGGTACCAGATGCTAAGTTAGAGACATCAGAAATATGTGGTAGTACA
480
P2-82_t3   > GAAATGCAATACAAGGTACCAGATGCTAAGTTAGAGACATCAGAAATATGTGGTAGTACA
480
CONSENSUS  > GaAaTGCAatACAaGgtACCAGatGCTaAGTtaGaGaCAtCAGAAaTATGtGGtAGTACA
480
```

```
P5-82_t7   < AAAA.GATCCAGTGTTGCACCAAACATAAGTCCTAAAGTAAGTCCTTTCAGATAATTAGA
117
P10-82_t7  < AAAA.GACCCAGGGATGCACCAAACAAAAGTCCTAAAGTAAGTCCTTCTAGAAAATTAGA
124
P8-82_t7   < AAAA.GATCCAGTGATGCACCAAACATAAGTCCTAAAGTAAGTCCTTTCAGATAATTAGA
128
P3-82_t7   < AAAA.GATCCAGTGATGCACCAAACATAAGTCCTAAAGTAAGCCCTTTCAGATAATTAGA
146
P1-82_t7   < AAA..GATCCAGGGA.GCACCAAACATAAGTCCTTAAGTAAGTCCTT.CAGATA.TTAGA
159
P7-82_t7   < AAAAAGATCCAGTGATGCACCAAACATAAGTCCTAAAGTAAGTCCTTTCAGATAATTAGA
163
P6-82_t7   < AAAA.GATCCAGTGATGCACCAAACATAAGTCCTAAAGTAAGTCCTTTCAGATAATTAGA
174
P4-82_t7   < AAAA.GATCCAGTGATGCACCAAACATAAGTGCTAAAGTAAGTCCTTTCAGATAATTAGA
191
P2-82_t7   < AAAA.GATCCAGTGATGCACCAAACATAAGTCCTAAAGTAAGTCCTTTCAGATAATTAGA
204
P6-82_t3   > AAAA.GATCCAGTGATGCACCAAACATAAGTCCTAAAGTAAGTCCTTTCAGATAATTAGA
529
P5-82_t3   > AAAA.GATCCAGTGATGCACCAAACATAAGTCCTAAAGTAAGTCCTTTCAGATAATTAGA
529
P7-82_t3   > AAAA.GATCCAGTGATGCACCAAACATAAGTCCTAAAGTAAGTCCTTTCAGATAATTAGA
534
P9-82_t3   > AAAA.GATCCAGTGATGCACCAAACATAAGTCCTAAAGTAAGTCCTTTCAGATAATTAGA
537
P1-82_t3   > AAAA.GATCCAGTGATGCACCAAACATAAGTCCTAAAGTAAGTCCTTTCAGATAATTAGT
537
P8-82_t3   > AAAA.GATCCAGTGATGCACCAAACATAAGTCCTAAAGTAAGTCCTTTCAGATAATTAGA
540
P10-82_t3  > AAAA.GATCCAGTGATGCACCAAACATAAGTCCTAAAGTAAGTCCTTTCAGATAATTAGA
540
P4-82_t3   > AAAA.GATCCAGTGATGCACCAAACATAAGTCCTAAAGTAAGTCCTTTCAGATAATTAGA
540
P3-82_t3   > AAAA.GATCCAGTGATGCACCAAACATAAGTCCTAAAGTAAGTCCTTTCAGATAATTAGA
540
P2-82_t3   > AAAA:.GATCCAGTGATGCACCAAACATAAGTCCTAAAGTAAGTCCTTTCAGATAATTAGA
540
CONSENSUS  > AAAa.GAtCCAGtGatGCACCAAACAtAAGTCCTaAAGTAAGtCCTTtcAGAtAaTTAGA
540

.........+.........+.........+.........+.........+.........+

P5-82_t7   < AATAGGCTAAGCAAAGCAATGGCAAAGAAAAAAAAAAA.GGTATAAAA.CTGATAGAAAA
177
P10-82_t7  < AATAGGCTAAGCAAAGCAATGGCAAAGAAAAAAAAAAAAGGTATAAAA.CTGATAGAAAA
184
P8-82_t7   < AATGGGCTAAGCAAAGCAATGGCAAAGAAAAAAAAAAAGGTATAAAA.CTGATAGAAAA
188
P3-82_t7   < AATAGGCTAAGCAAAGCAATGGCAAAGAAAAAAAAAAAAGGTATAAAA.CTGATAGAAAA
206
P1-82_t7   < AATAGGCTAAGCAAAGCAATGGCAAAGAAAAAAAAAA...GGTATAAAA.CTGATAGAAAA
219
P7-82_t7   < AATAGGCTAAGCAAAGCAATGGCAAAGAAAAAAAAAAA...GGTATAAAAACTGATAGAAAA
223
P6-82_t7   < AATAGGCTAAGCAAAGCAATGGCAAAGAAAAAAAAAAAAGGTATAAAA.CTGATAGAAAA
234
P4-82_t7   < AATAGGCTAAGCAAAGCAATGGCAAAGAAAAAAAAAAA.GGTATAAAA.CTGATAGAAAA
251
P2-82_t7   < AATAGGCTAAGCAAAGCAATGGCAAAGAAAAAAAAAAA..GGTATAAAA.CTGATAGAAAA
264
P6-82_t3   > AATAGGCTAAGCAAAGCAATGGCAAAGAAAAAAAAAAAAGGTATAAAA.CTGATAGAAAA
589
```

FIGURE 1 CONTINUED

```
P5-82_t3    > AATAGGCTAAGCAAAGCAATGGCAAAG.AAAAAAAAAAGGTATAAAA.CTGATAGAAAA
589
P7-82_t3    > AATAGGCTAAGCAAAGCAATGGCAAAG..AAAAAAAAAAGGTATAAAA.CTGATAGAAAA
594
P9-82_t3    > AATAGGCTAAGCAAAGCAATGGCAAAGAAAAAAAAAAAGGTATAAAA.CTGATAGAAAA
597
P1-82_t3    > AATAGGCTAAGCAAAGCAATGGCAAAG..AAAAAAAAAAGGTATAAAA.CTGATAGAAAA
597
P8-82_t3    > AATGGGCTAAGCAAAGCAATGGCAAAGAAAAAAAAAAAGGTATAAAA.CTGATAGAAAA
600
P10-82_t3   > AATAGGCTAAGCAAAGCAATGGCAAAGAAAAAAAAAAAGGTATAAAA.CTGATAGAAAA
600
P4-82_t3    > AATAGGCTAAGCAAAGCAATGGCAAAG..AAAAAAAAAAGGTATAAAA.CTGATAGAAAA
600
P3-82_t3    > AATAGGCTAAGCAAAGCAATGGCAAAGAAAAAAAAAAAGGTATAAAA.CTGATAGAAAA
600
P2-82_t3    > AATAGGCTAAGCAAAGCAATGGCAAAG..AAAAAAAAAAGGTATAAAA.CTGATAGAAAA
600
CONSENSUS   > AATaGGCTAAGCAAAGCAATGGCAAAGaaAAAAAAAAaaGGTATAAAA.CTGATAGAAAA
600
```

SEQ ID NO:           .........+.........+.........+.........+.........+.........+

```
41  P9-82_t7    <                                              AGTTTAAAAGAATTTAAAAAATTT
    24
    P5-82_t7    < ATGACAAGAGAAACAGAGAAACCAAAACTGCAAGTCAGTTTTAAAGAATTTAATAATTTT
    237
    P10-82_t7   < ATGACAAAAGAAACAGAGAAACCAAAACTGCAAGTCAGTTTTAAAGAATTTAATAATTTT
    244
    P8-82_t7    < ATGACAAAAGAAACAGAGAAACCAAAACTGCAAGTCAGTTTTAAAGAATTTAATAATTTT
    248
    P3-82_t7    < ATGACAAAAGAAACAGAGAAACCAAAACTGCAAGTCAGTTTTAAAGAATTTAATAATTTT
    266
    P1-82_t7    < ATGACAAAAGAAACAGAGAATCCAAAACTTCAAGTCAGTTTTAAAGAATTTAATAATTTT
    279
    P7-82_t7    < ATGACAAAAGAAACAGAGAAACCAAAACTGCAAGTCAGTTTTAAAGAATTTAATAATTTT
    283
    P6-82_t7    < ATGACAAAAGAAACAGAGAAACCAAAACTGCAAGTCAGTTTTAAAGAATTTAATAATTTT
    294
    P4-82_t7    < .ATGACAAAAGAAACAGAGAAACCAAAACTGCAAGTCAGTTTTAAAGAATTTAATAATTTT
    311
    P2-82_t7    < ATGACAAAAGAAACAGAGAAACCAAAACTGCAAGTCAGTTTTAAAGAATTTAATAATTTT
    324
    P6-82_t3    > ATGACAAAAGAAACAGAGAAACCAAAACTGCAAGTCAGTTTTAAAGAATTTAATAATTTT
    649
    P5-82_t3    > ATGACAAGAGAAACAGAGAAACCAAAACTGCAAGTCAGTTTTAAAGAATTTAATAATTTT
    649
    P7-82_t3    > ATGACAAAAGAAACAGAGAAACCAAAACTGCAAGTCAGTTTTAAAGAATTTAATAATTTT
    654
    P9-82_t3    > ATGACAAAAGAAACAGAGAAACCAAAACTGCAAGTCAGTTTTAAAGAATTTAATAATTTT
    657
    P1-82_t3    > ATGACAAAAGAAACAGAGAAACCAAAACTGCAAGTCAGTTTTAAAGAATTTAATAATTTT
    657
    P8-82_t3    > ATGACAAAAGAAACAGAGAAACCAAAACTGCAAGTCAGTTTTAAAGAATTTAATAATTTT
    660
    P10-82_t3   > ATGACAAAAGAAACAGAGAAACCAAAACTGCAAGTCAGTTTTAAAGAATTTAATAATTTT
    660
    P4-82_t3    > ATGACAAAAGAAACAGAGAAACCAAAACTGCAAGTCAGTTTTAAAGAATTTAATAATTTT
    660
    P3-82_t3    > ATGACAAAAGAAACAGAGAAACCAAAACTGCAAGTCAGTTTTAAAGAATTTAATAATTTT
    660
    P2-82_t3    > ATGACAAAAGAAACAGAGAAACCAAAACTGCAAGTCAGTTTTAAAGAATTTAATAATTTT
    660
```

FIGURE 1 CONTINUED

```
CONSENSUS  > ATGACAAAAGAAACAGAGAAaCCAAAACTgCAAGTCAGTTTtAAAGAATTTAAtAAtTTT
660

.........+.........+.........+.........+.........+.........+
P9-82_t7   < AGCAATTTCTTATCGTATCAGCCCTATTGCCATTTTGCAAAATGATTTTGTTTAATAAAA
84
P5-82_t7   < AGCGATTTCTTAACGTATCAGCCC.ATTGTCATTTTGCATAATGATTTTGTTTTATTAAA
297
P10-82_t7  < AGCAATTTCTTAACGTATCAGCCC.ATTGTCATTTTGCATAATGATTTTGTTTTATTAAA
304
P8-82_t7   < AGCAATTTCTTAACGTATCAGCCC.ATTGTCATTTTGCATAATGATTTTGTTTTATTAAA
308
P3-82_t7   < AGCGATTTCTTAACGTATCAGCCC.ATTGTCATTTTGCATAATGATTTTGTTTTATTAAA
326
P1-82_t7   < AGCGATTTCTTAACGTATCAGCCC.ATTGTCATTTTGCATAATGATTTTGTTTAATTAAA
339
P7-82_t7   < AGCAATTTCTTAACGTATCAGCCC.ATTGTCATTTTGCATAATGATTTTGTTTTATTAAG
343
P6-82_t7   < AGCAATTTCTTAACGTATCAGCCC.ATTGTCATTTTGCATAATGATTTTGTTTTATTAAA
354
P4-82_t7   < AGCGATTTCTTAACGTATCAGCCC.ATTGTCATTTTGCATAATGATTTTGTTTTATTAAA
371
P2-82_t7   < AGCGATTTCTTAACGTATCAGCCC.ATTGTCATTTTGCATAATGATTTTGTTTTATTAAA
384
P6-82_t3   > AGCAATTTCTTAACGTATCAGCCC.ATTGTCATTTTGCATAATGATTTTGTTTTATTAAA
709
P5-82_t3   > AGCGATTTCTTAACGTATCAGCCC.ATTGTCATTTTGCATAATGAtTTTGTTTTATTAAA
709
P7-82_t3   > AGCAATTTCTTAACGTATCAGCCC.ATTGTCATTTTGCATAATGATTTTGTTTTATTAAG
714
P9-82_t3   > AGCAATTTCTTAACGTATCAGCCC.ATTGTCATTTTGCATAATGATTTTGTTTTATTAAA
717
P1-82_t3   > AGCGATTTCTTAACGTATCAGCCC.ATTGTCATTTTGCATAATGATTTTGTTTTATTAAA
717
P8-82_t3   > AGCAATTTCTTAACGTATCAGCCC.ATTGTCATTTTGCATAATGATTTTGTTTTATTAAA
720
P10-82_t3  > AGCAATTTCTTAACGTATCAGCCC.ATTGTCATTTTGCATAATGATTTTGTTTTATTAAA
720
P4-82_t3   > AGCGATTTCTTAACGTATCAGCCC.ATTGTCATTTTGCATAATGATTTTGTTTTATTAAA
720
P3-82_t3   > AGCGATTTCTTAACGTATCAGCCC.ATTGTCATTTTGCATAATGATTTTGTTTTATTAAA
720
P2-82_t3   > AGCGATTTCTTAACGTATCAGCCC.ATTGTCATTTTGCATAATGATTTTGTTTTATTAAA
720
CONSENSUS  > AGCrATTTCTTAaCGTATCAGCCC.ATTGtCATTTTGCAtAATGATTTTGTTTtATtAAa
720

.........+.........+.........+.........+.........+.........+
P9-82_t7   < ATCTAGATTTCAATTAGGTTAAAGGGTTTTAGGTGCAGGAAGCAATAACATTTTATGTTT
144
P5-82_t7   < ATCTAGATTTCAATTAGGTTAAAGGGTTTTAGGTGCAGGAAGCAATAACATTTTATGTTT
357
P10-82_t7  < ATCTAGATTTCAATTAGGTTAAAGGGTTTTAGGTGCAGGAAGCAATAACATTTTATGTTT
364
P8-82_t7   < ATCTAGATTTCAATTAGGTTAAAGGGTTTTAGGTGCAGGAAGCAATAACATTTTATGTTT
368
P3-82_t7   < ATCTAGATTTCAATTAGGTTAAAGGGTTTTAGGTGCAGGAAGCAATAACATTTTATGTTT
386
P1-82_t7   < ACCTAGATTCCAATTAGGTTAAAGGGTTTTAGGTGCAGGAAGCAATAACATTTTATGTTT
399
```

FIGURE 1 CONTINUED

```
P7-82_t7   < ATCTAGATTTCAATTAGGTTAAAGGGTTTTAGGTGCAGGAAGCAATAACATTTTATGTTT
403
P6-82_t7   < ATCTAGATTTCAATTAGGTTAAAGGGTTTTAGGTGCAGGAAGCAATAACATTTTATGTTT
414
P4-82_t7   < ATCTAGATTTCAATTAGGTTAAAGGGTTTTAGGTGCAGGAAGCAATAACATTTTATGTTT
431
P2-82_t7   < ATCTAGATTTCAATTAGGTTAAAGGGTTTTAGGTGCAGGAAGCAATAACATTTTATGTTT
444
P6-82_t3   > ATCTAGATTTCAATTAGGTTAAAGGGTTTTAGGTGCAGGAAGCAATAACATTTTATGTTT
769
P5-82_t3   > ATCTAGATTTCAATTAGGTTAAAGGGTTTTAGGTGCAGGAAGCAATAACATTTTATGTTT
769
P7-82_t3   > ATCTAGATTTCAATTAGGTTAAAGGGTTTTAGGTGCAGGAAGCAATAACATTTTATGTTT
774
P9-82_t3   > ATCTAGATTTCAATTAGGTTAAAGGGTTTTAGGTGCAGGAAGCAATAACATTTTATGTTT
777
P1-82_t3   > ATCTAGATTTCAATTAGGTTAAAGGGTTTTAGGTGCAGGAAGCAATAACATTTTATGTTT
777
P8-82_t3   > ATCTAGATTTCAATTAGGTTAAAGGGTTTTAGGTGCAGGAAGCAATAACATTTTATGTTT
780
P10-82_t3  > ATCTAGATTTCAATTAGGTTAAAGGGTTTTAGGTGCAGGAAGCAATAACATTTTATGTTT
780
P4-82_t3   > ATCTAGATTTCAATTAGGTTAAAGGGTTTTAGGTGCAGGAAGCAATAACATTTTATGTTT
780
P3-82_t3   > ATCTAGATTTCAATTAGGTTAAAGGGTTTTAGGTGCAGGAAGCAATAACATTTTATGTTT
780
P2-82_t3   > ATCTAGATTTCAATTAGGTTAAAGGGTTTTAGGTGCAGGAAGCAATAACATTTTATGTTT
780
CONSENSUS  > AtCTAGATTtCAATTAGGTTAAAGGGTTTTAGGTGCAGGaAGCAATAACATTTTATGTTT
780

.........+.........+.........+.........+.........+.........+

P9-82_t7   < AATAAGTTATTTAGAAAATAAGAATAATTAAAATGTTCCTTCAAAGTTGCTGAAGTGTAA
204
P5-82_t7   < AATAAGTTATTTAGAAAATAAGAATAATT.AAATGTTCCTTCAAAGTTGCTGAAGTGTAA
417
P10-82_t7  < AATAAGTTATTTAGAAAATAAGAATAATT.AAATGTTCCTTCAAAGTTGCTGAAGTGTAA
424
P8-82_t7   < AATAAGTTATTTAGAAAATAAGAATAATT.AAATGTTCCTTCAAAGTTGCTGAAGTGTAA
428
P3-82_t7   < AATAAGTTATTTAGAAAATAAGAATAATT.AAATGTTCCTTCAAAGTTGCTGAAGTGTAA
446
P1-82_t7   < AAAAATTTATTTAGAAA.TAAGAAAAATT.AAATGTTCCTTCAAAGTTGCTGAAGTGTAA
459
P7-82_t7   < AATAAGTTATTTAGAAAATAAGAATAATT.AAATGTTCCTTCAAAGTTGCTGAAGTGTAA
463
P6-82_t7   < AATAAGTTATTTAGAAAATAAGAATAATT.AAATGTTCCTTCAAAGTTGCTGAAGTGTAA
474
P4-82_t7   < AATAAGTTATTTAGAAAATAAGAATAATT.AAATGTTCCTTCAAAGTTGCTGAAGTGTAA
491
P2-82_t7   < AATAAGTTATTTAGAAAATAAGAATAATT.AAATGTTCCTTCAAAGTTGCTGAAGTGTAA
504
P6-82_t3   > AATAAGTTATTTAGAAAATAAGAATAATT.AAATGTTCCTTCAAAGTTGCTGAAGTGTAA
829
P5-82_t3   > AATAAGTTATTTAGAAAATAAGAATAATT.AAATGTTCCTTCAAAGTTGCTGAAGTGTAA
829
P7-82_t3   > AATAAGTTATTTAGAAAATAAGAATAATT.AAATGTTCCTTCAAAGTTGCTGAAGTGTAA
834
P9-82_t3   > AATAAGTTATTTAGAAAATAAGAATAATT..AATGTTCCTTCAAAGTTGCTGAAGTGT.A
837
P1-82_t3   > AATAAGTTATTTAG.AAATAAGAATAATT.AAATGTTCCTTCAAAGTTGCTGAAGTGTAA
837
```

FIGURE 1 CONTINUED

```
P8-82_t3    >  AATAAGTTATTTAGAAAATAAGAATAATT.AAATGTTCCTTCAAAGTTGCTGAAGTGTAA
840
P10-82_t3   >  AATAAGTTATTTAGAAAATAAGAATAATT.AAATGTTCCTTCAAAGTTGCTGAAGTGTAA
840
P4-82_t3    >  AATAAGTTATTTAGAAAATAAGAATAATT.AAATGTTCCTTCAAAGTTGCTGAAGTGTAA
840
P3-82_t3    >  AATAAGTTATTTAGAAAATAAGAATAATT.AAATGTTCCTTCAAAGTTGCTGAAGTGTAA
840
P2-82_t3    >  AATAAGTTATTTAGAAAATAAGAATAATT.AAATGTTCCTTCAAAGTTGCTGAAGTGTAA
840
CONSENSUS   >  AAtAAgTTATTTAGaAAaTAAGAAtAATT.aAATGTTCCTTCAAAGTTGCTGAAGTGTaA
840

.........+.........+.........+.........+.........+.........+

P9-82_t7    <  ATATTTACCACTTTA.TAAATAAATATTAATACTACTTTTATTTGTT.GGGTTAAAGAAA
264
P5-82_t7    <  ATATTTACCACTTTA.TAAATAAATATTAATACTACTTTTATTTGTT.GGGTTAAAGAAA
477
P10-82_t7   <  ATATTTACCACTTTA.TAAATAAATATTAATACTACTTTTATTTGTT.GGGTTAAAGAAA
484
P8-82_t7    <  ATATTTACCACTTTA.TAAATAAATATTAATACTACTTTTATTTGTT.GGGTTAAAGAAA
488
P3-82_t7    <  ATATTTACCACTTTA.TAAATAAATATTAATACTACTTTTATTTGTTTGGGTTAAAGAAA
506
P1-82_t7    <  ATATTTACCACTTTA.TAAATAAATATTAATACTACTTTTATTTGTT.GGGTTAAAGAAA
519
P7-82_t7    <  ATATTTACCACTTTA.TAAATAAATATTAATACTACTTTTATTTGTT.GGGTTAAAGAAA
523
P6-82_t7    <  ATATTTACCACTTTA.TAAATAAATATTAATGCTACTTTTATTTGTT.GGGTTAAAGAAA
534
P4-82_t7    <  ATATTTACCACTTTA.TAAATAAATATTAATGCTACTTTTATTTGTT.GGGTTAAAGAAA
551
P2-82_t7    <  ATATTTACCACTTTA.TAAATAAATATTAATACTACTTTTATTTGTT.GGGTTAAAGAAA
564
P6-82_t3    >  ATATTTACCACTTTA.TAAATAAATATTAATGCTACTTTTATTTGTT.GGGTTAAAGAAA
889
P5-82_t3    >  ATATTTACCACTTTA.TAAATAAATATTAATACTACTTTTATTTGTT.GGGTTAAAGAAA
889
P7-82_t3    >  ATATTTACCACTTTA.TAAATAAATATTAATACTACTTTTATTTGTT.GGGTTAAAGAAA
894
P9-82_t3    >  ATATTTACCACTTTATTAAATAATTATT.ATTCTACTTTTTTTTGTT.GGGTTTAAGGAA
897
P1-82_t3    >  ATATTTACCACTTTA.TAAATAAATATTTATACTACTTTTATTTGTT.GGGTTAAAGAAA
897
P8-82_t3    >  ATATTTACCACTTTA.TAAATAAATATTAATACTACTTTTATTTGTT.GGGTTAAAGAAA
900
P10-82_t3   >  ATATTTACCACTTTA.TTAATAAATATTAATACTACTTTTATTTGTT.GGGTTAAAGAAA
900
P4-82_t3    >  ATATTTACCACTTTA.TAAATAAATATTAATGCTACTTTTATTTGTT.GGGTTAAAGAAA
900
P3-82_t3    >  ATATTTACCACTTTA.TAAATAAATATTAATACTACTTTTATTTGTT.GGGTTAAAGAAA
900
P2-82_t3    >  ATATTTACCACTTTA.TAAATAAATATTAATACTACTTTTATTTGTT.GGGTTAAAGAAA
900
CONSENSUS   >  ATATTTACCACTTTA.TaAATAAaTATTaATaCTACTTTTaTTTGTT.GGGTTaAAGaAA
900

.........+.........+.........+.........+.........+.........+

P9-82_t7    <  CTGGCTATCAGTTTTCACTCAAACAGTAAATTATTTCACAAACAGTTATTAAAATCCTAC
324
P5-82_t7    <  TTGGCTATCAGTTTTCACTCAAACAGTAAATTATTTCACAAACAGTTATTAAAATCCTAC
537
```

FIGURE 1 CONTINUED

```
P10-82_t7  < CTGGCTATCAGTTTTCACTCAAACAGTAAATTATTTCACAAACAGTTATTAAAATCCTAC
544
P8-82_t7   < CTGGCTATCAGTTTTCACTCAAACAGTAAATTATTTCACAAACAGTTATTAAAATCCCAC
548
P3-82_t7   < CTGGCTATCAGTTTTCACTCAAACATTAAATTATTTCACAAACAGTTATTAAAATCCTAC
566
P1-82_t7   < CTGGCTATCAG.TTTCACTCAAACATTAAATTATTTCACAAACAGTTATTAAAATCCTAC
579
P7-82_t7   < CTGGCTATCAGTTTTCACTCAAACAGTAAATTATTTCACAAACAGTTATTAAAATCCTAC
583
P6-82_t7   < CTGGCTATCAGTTTTCACTCAAACAGTAAATTATTTCACAAACAGTTATTAAAATCCTAC
594
P4-82_t7   < CTGGCTATCAGCTTTCACTCAAACATTAAATTATTTCACAAACAGTTATTAAAATCCTAC
611
P2-82_t7   < CTGGCTATCAGTTTTCACTCAAACATTAAATTATTTCACAAACAGTTATTAAAATCCTAC
624
P6-82_t3   > CTGGCTATCAGTTTTCACTCAAACAGTAAATTATTTCACAAACAGTTATTAAAATCCTAC
949
P5-82_t3   > TTGGCTATCAGTTTTCACTCAAACATTAAATTATTTCACAAACAGTTATTAAAATCCTAC
949
P7-82_t3   > CTGGCTATCAGTTTTCACTCAAACAGTAAATTATTTCACAAACAGTTATTAAAATCCTAC
954
P9-82_t3   > CTGGCTTTCAGTTTTCACT
916
P1-82_t3   > CTGGCTATCAGTTTTCACTCAAACATTAATTTTTTCACAAACAGTTTTTTAAATCCTAC
957
P8-82_t3   > CTGGCTATCAGTTTTCACTCAAACAGTAAATTATTTCACAAACAGTTATTAAAATCCCAC
960
P10-82_t3  > CTGGCTATCAGTTTTCACTCAAACAGTAAATTATTTCACAAACAGTTATTAAAATCCTAC
960
P4-82_t3   > CTGGCTATCAGCTTTCACTCACACATTAAATTATTTCACAAACAGTTATT.AAATCCTAC
960
P3-82_t3   > CTGGCTATCAGTTTTCACTCAAACATTAAATTATTTCACAAACAGTTATTAAAATCCTAC
960
P2-82_t3   > CTGGCTATCAGTTTTCACTCAAACATTAAATTATTTCACAAACAGTTATTAAAATCCTAC
960
CONSENSUS  > CTGGCTaTCAGtTTTCACTCAaACAtTaAATTaTTTCACAAACAGTTaTTaAAATCCtAC
960

.........+.........+.........+.........+.........+.........+

P9-82_t7   < CATGTGCTAAGTTATCATACTGAACACTAGAAAATATTAATAATAGTTACAAATAATAGC
384
P5-82_t7   < CATGTGCTAAGTTATCATACTGAACACTAGAAAATATTAATAATAGTTACAAATAATAGC
597
P10-82_t7  < CATGTGCTAAGTTATCATACTGAACACTAGAAAATATTAATAATAGTTACAAATAATAGC
604
P8-82_t7   < CATGTGCTAAGTTATCATACTGAACACTAGAAAATATTAATAATAGTTACAAATAATAGC
608
P3-82_t7   < CATGTGCTAAGTTATCATACTGAACACTAGAAAATATTAATAATAGTTACAAATAATAGC
626
P1-82_t7   < CATGTGCTAAGTTATCATACTGAACACTAGAAAATATTAATAATAGTTACAAATAATAGC
639
P7-82_t7   < CATGTGCTAAGTTATCATACTGAACACTAGAAAATATTAATAATAGTTACAAATAATAGC
643
P6-82_t7   < CATGTGCTAAGTTATCATACTGAACACTAGAAAATATTAATAATAGTTACAAATAATAGC
654
P4-82_t7   < CATGTGCTAAGTTATCATACTGAACACTAGAAAATATTAATAATAGTTACAAATAATAGC
671
P2-82_t7   < CATGTGCTAAGTTATCATACTGAACACTAGAAAATATTAATAATAGTTACAAATAATAGC
684
P6-82_t3   > CATGTGCTAAGTTATCATACTGAACACTAGAAAATATTAATAATAGTTACAAATAATAGC
1009
```

FIGURE 1 CONTINUED

```
P5-82_t3    > CATGTGCTAAGTTATCATACTGAACACTAG.AAATATTAATAATAGTTACAAATAATAGC
1009
P7-82_t3    > CATGTGCTAAGTTATCATACTGAACACTAGAAAATATTAATAATAGTTACAAATAATAGC
1014
P1-82_t3    > CATGTGCTAAGTTTTCATACTGAACACTAGAAAATATTAATAATAGTTACAAATAATAGC
1017
P8-82_t3    > CATGTGCTAAGTTATCATACTGAACACTAGAAAATATTAATAATAGTTACAAATAATAGC
1020
P10-82_t3   > CATGTGCTAAGTTATCATACTGAACCCTAGAAAATATTAATAATAGTTACCAATAATAGC
1020
P4-82_t3    > CATGTGCTAAGTTATCATACTGAACACTAG.AAATATTAATAATAGTTAC.AATAATAGC
1020
P3-82_t3    > CATGTGCTAAGTTATCATACTGAACACTAGAAAATATTAATAATAGTTACAAATAATAGC
1020
P2-82_t3    > CATGTGCTAAGTTATCATACTGAACACTAGAAAATATTAATAATAGTTACAAATAATAGC
1020
CONSENSUS   > CATGTGCTAAGTTaTCATACTGAACaCTAGaAAATATTAATAATAGTTACaAATAATAGC
1020

.........+.........+.........+.........+.........+.........+

P9-82_t7    < ATTTT.GGATACATGTATATGCATGGCTGAATCCCTTTGCTGTTCACTTGAAACTAGCAC
444
P5-82_t7    < ATTTT.GGATACATGTATATGCATGGCTGAATCCCTTTGCTGTTCACTTGAAACTACCAC
657
P10-82_t7   < ATTTT.GGATACATGTATATGCATGGCTGAATCCCTTTGCTGTTCACTTGAAACTACCAC
664
P8-82_t7    < ATTTT.GGATACATGTATATGCATGGCTGAATCCCTTTGCTGTTCACTTGAAACTACCAC
668
P3-82_t7    < ATTTT.GGATACATGTATATGCATGGCTGAATCCCTTTGCTGTTCACTTGAAACTACCAC
686
P1-82_t7    < ATTTT.GGATACATGTATATGCATGGCTGAATCCCTTTGCTGTTCACTTGAAACTACCAC
699
P7-82_t7    < ATTTT.GGATACATGTATATGCATGGCTGAATCCCTTTGCTGTTCACTTGAAACTACCAC
703
P6-82_t7    < ATTTT.GGATACATGTATATGCATGGCTGAATCCCTTTGCTGTTCACTTGAAACTACCAC
714
P4-82_t7    < ATTTT.GGATACATGTATATGCATGGCTGAATCCCTTTGCTGTTCACTTGAAACTACCAC
731
P2-82_t7    < ATTTT.GGATACATGTATATGCATGGCTGAATCCCTTTGCTGTTCACTTGAAACTACCAC
744
P6-82_t3    > ATTTT.GGATACATGTATATGCATGGCTGGATCCCTTTGCTGTTCACTTGAAACTACCAC
1069
P5-82_t3    > ATTTT.GGATACATGTATATGCATGGCTGAATCCCTTTGCTGTTCACTTGAAACTACCAC
1069
P7-82_t3    > ATTTT.GGATACATGTATATGCATGGCTGGATCCCTTTGCTGTTCACTTGAAACTACCAC
1074
P1-82_t3    > ATTTT.GGATACATGTATATGCATGGCTGAATCCCTTTGCTGATCCCTTGAAACTACCAC
1077
P8-82_t3    > ATTT..GGATACATGTATATGCATGGCTGAATCCCTTTGCTGTTCACTTGAAACTACCCC
1080
P10-82_t3   > CTTTTAGGATACCTGTATATGCCTGGCTGAATCCCTTTGCTGTTCCCTTGAAACTACCCC
1080
P4-82_t3    > ATTTT.GGGTACATGTATATGCATGGCTGGATCCCTTTGCTGTTCACTTGAAACTACCAC
1080
P3-82_t3    > ATTTT.GGGTACATGTATATGCATGGCTGAATCCCTTTGCTGTTCACTTGAAACTACCCC
1080
P2-82_t3    > ATTTT.GGATACATGTATATGCATGGCTGAATCCCTTTGCTGTTCACTTGAAACTACCAC
1080
CONSENSUS   > aTTTt.GGaTACaTGTATATGCaTGGCTGaATCCCTTTGCTGttCaCTTGAAACTACCaC
1080
```

FIGURE 1 CONTINUED

```
            ..........+..........+..........+..........+..........+..........+
P9-82_t7    < AACATTGTTAATCAAATATATCCCAATACAAAATAAATTTTAAAGTTTGAAAAAAATAAT
504
P5-82_t7    < AACATTGTTAATCAAATATATCCCAATACAAAATAAATTTTAAAGTTTGAAAAAAATAAT
717
P10-82_t7   < AACATTGTTAATCAAATATATCCCAATACAAAATAAATTTTAAAGTTTGAAAAAAATAAT
724
P8-82_t7    < AACATTGTTAATCAAATATATCCCAATACAAAATAAATTTTAAAGTTTGAAAAAAATAAT
728
P3-82_t7    < AACATTGTTAATCAAATATATCCCAATACAAAATAAATTTTAAAGTTTGAAAAAAATAAT
746
P1-82_t7    < AACATTGTTAATCAAATATATCCCAATACAAAATAAATTTTAAAGTTTGAAAAAAATAAT
759
P7-82_t7    < AACATTGTTAATCAAATATATCCCAATACAAAATAAGTTTTAAAGTTTGAAAAAAATAAT
763
P6-82_t7    < AACATTGTTAATCAAATATATCCCAATACAAAATAAATTTTAAAGTTTGAAAAAAATAAT
774
P4-82_t7    < AACATTGTTAATCAAATATATCCCAATACAAAATAAATTTTAAAGTTTGAAAAAAATAAT
791
P2-82_t7    < AACATTGTTAATCAAATATATCCCAATACAAAATAAATTTTAAAGTTTGAAAAAAATAAT
804
P6-82_t3    > AACATTGTTAATC
1082
P5-82_t3    > AACATTGTTAATCCAATATATCCCCATACCAAATATATTTTAAAGTTTGGAAAAAAT
1126
P7-82_t3    > AACATTGTTAATCAAATATATCCCAATAC.AAATAAGTTTTA
1116
P1-82_t3    > AACATTGTTAATCAAATATATCCC.ATACAAAATAAATTTTAAAGATTGAAAAAAATAAT
1137
P8-82_t3    > AACATTGTT.ATCAAATATATCCCAATACCAAATAAATTTAAAAGATTG
1129
P10-82_t3   > AACATTGTAAATC.AATATATCCCCATACAAAATAAATTTTAAAGTTTGG
1130
P4-82_t3    > AACATTGTTAATC.AATATATCCCAATACAAAATAAATTTT.AAGTTTGAAAAAAATAAT
1140
P3-82_t3    > AACATTGTTAATCCAATATATCCCAATACACAATAAATTTTAAAGTTTGAAAAAAATAATA
1140
P2-82_t3    > AACATTGTT.ATCAAATATATCCCAATACAAAATATATTTTAAAGTTTGGAAAAATAAAT
1140
CONSENSUS   > AACATTGTtaATCaAATATATCCCaATACaaAATAaaTTTtaAAGtTTGaAAAAAatAat
1140
            ..........+..........+..........+..........+..........+..........+

P9-82_t7    < AACATTCTGCTAAACTAGTATGGATGAGTATGTGTGGGTTCTGTATATAGACATACATTA
564
P5-82_t7    < AACATTCTGCTAAACTAGTATGGATGAGTATGTGTGGGTTCTGTATATAGACATACATTA
777
P10-82_t7   < AACATTCTGCTAAACTAGTATGGATGAGTATGTGTGGGTTCTGTATATAGACATACATTA
784
P8-82_t7    < AACATTCTGCTAAACTAGTATGGATGAGTATGTGTGGGTTCTGTATATAGACATACATTA
788
P3-82_t7    < AACATTCTGCTAAACTAGTATGGATGAGTATGTGTGGGTTCTGTATATAGACATACATTA
806
P1-82_t7    < AACATTCTGCTAAACTAGTATGGATGAGTATGTGTGGGTTCTGTATATAGACATACATTA
819
P7-82_t7    < AACATTCTGCTAAACTAGTATGGATGAGTATGTGTGGGTTCTGTATATAGACATACATTA
823
P6-82_t7    < AACATTCTGCTAAACTAGTATGGATGAGTATGTGTGGGTTCTGTATATAGACATACATTA
834
P4-82_t7    < AACATTCTGCTAAACTAGTATGGATGAGTATGTGTGGGTTCTGTATATAGACATACATTA
851
```

FIGURE 1 CONTINUED

```
P2-82_t7    <  AACATTCTGCTAAACTAGTATGGATGAGTATGTGTGGGTTCTGTATATAGACATACATTA
864
P1-82_t3    >  .ACATTCTGCTAACCTAGTATGGATGGGTATGTGTGGG.TCCGTATAT.GGCATCCA.TA
1197
P3-82_t3    >  .ACATTCTGCTAA
1153
P2-82_t3    >  .ACATTCTGCTAAACTAGTATGGGTGGGTATGTGTGGGTTCTGTATATAGGCATACATTA
1200
CONSENSUS   >  aACATTCTGCTAAaCTAGTATGGaTGaGTATGTGTGGGtTCtGTATATaGaCATaCAtTA
1200

.........+.........+.........+.........+.........+.........+

P9-82_t7    <  TTTCTTGAATATAGATCGATAGGTAATGTAGTATTCTGTTTTCCTTTTCAGGTTGGACTG
624
P5-82_t7    <  TTTCTTGAATATAGATCGATAGGTAATGTAGTATTCTGTTTTCCTTTTCAGGTTGGACTG
837
P10-82_t7   <  TTTCTTGAATATAGATCGATAGGTAATGTAGTATTCTGTTTTCCTTTTCAGGTTGGACTG
844
P8-82_t7    <  TTTCTTGAATATAGATCGATAGGTAATGTAGTATTCTGTTTTCCTTTTCAGGTTGGACTG
848
P3-82_t7    <  .TTTCTTGAATATAGATCGATAGGTAATGTAGTATTCTGTTTTCCTTTTCAGGTTGGACTG
866
P1-82_t7    <  .TTTCTTGAATATAGATCGATAGGTAATGTAGTATTCTGTTTTCCTTTTCAGGTTGGACTG
879
P7-82_t7    <  TTTCTTGAATATAGATCGATAGGTAATGTAGTATTCTGTTATCCTTTTCAGGTTGGACTG
883
P6-82_t7    <  .TTTCTTGAATATAGATCGATAGGTAATGTAGTATTCTGTTTTCCTTTTCAGGTTGGACTG
894
P4-82_t7    <  TTTCTTGAATATAGATCGATAGGTAATGTAGTATTCTGTTTTCCTTTTCAGGTTGGACTG
911
P2-82_t7    <  TTTCTTGAATATAGATCGATAGGTAATGTAGTATTCTGTTTTCCTTTTCAGGTTGGACTG
924
P1-82_t3    >  ATTCTTG.AT.TTGGTCGATGGGT.ATGTAGTA.TCCGATTTCC.TTTCCGGTAGG.CAG
1257
P2-82_t3    >  TTTCTTGAATATAGGTCGGTGGGTAATG
1228
CONSENSUS   >  tTTCTTGaATaTaGaTCGaTaGGTaATGTAGTAtTCtGtTtTCCtTTTCaGGTtGGaCtG
1260

.........+.........+.........+.........+.........+.........+

P9-82_t7    <  GAAAATCTATCTTCTACAGTTTCATATCTACCACTTTACTTCATACAACCAGCATGTTTG
684
P5-82_t7    <  GAAAATCTATCTTCTACAGTTTCATATCTACCACTTTACTTCATACAACCAGCATGTTTG
897
P10-82_t7   <. GAAAATCTATCTTCTACAGTTTCATATCTACCACTTTACTTCATACAACCAGCATGTTTG
904
P8-82_t7    <  GAAAATCTATCTTCTACAGTTTCATATCTACCACTTTACTTCATACAATCAGCATGTTTG
908
P3-82_t7    <  GAAAATCTATCTTCTACAGTTTCATATCTACCACTTTACTTCATACAACCAGCATGTTTG
926
P1-82_t7    <  GAAAATCTATCTTCTACAGTTTCATATCTACCACTTTACTTCATACAACCAGCATGTTTG
939
P7-82_t7    <  GAAAATCTATCTTCTACAGTTTCATATCTACCACTTTACTTCATACAACCAGCATGTTTG
943
P6-82_t7    <  GAAAATCTATCTTCTACAGTTTCATATCTACCACTTTACTTCATACAACCAGCATGTTTG
954
P4-82_t7    <  GAAAATCTATCTTCTACAGTTTGATATCTACCACTTTACTTCATACAACCAGCATGTTTG
971
P2-82_t7    <  GAAAATCTATCTTCTACAGTTTCATATCTACCACTTTACTTCATACAACCAGCATGTTTG
984
P1-82_t3    >  Gg
1259
```

FIGURE 1 CONTINUED

```
CONSENSUS   > GaAAATCTATCTTCTACAGTTTCATATCTACCACTTTACTTCATACAAcCAGCATGTTTG
1320
              .........+.........+.........+.........+.........+.........+
P9-82_t7    < GAGTGGTGCATCAATAAGACAAATCGCAGAGTATTTCCTGAATTATTTATACTCTCCCTG
744
P5-82_t7    < GAGTGGTGCATCAATAAGACAAATCGCAGAGTATTTCCTGAATTATTTATACTCTCTCTG
957
P10-82_t7   < GAGTGGTGCATCAATAAGACAAATCGCAGAGTATTTCCTGAATTATTTATACTCTCCCTG
964
P8-82_t7    < GAGTGGTGCATCAATAAGACAAATCGCAGAGTATTTCCTGAATTATTTATACTCTCCCTG
968
P3-82_t7    < GAGTGGTGCATCAATAAGACAAATCGCAGAGTATTTCCTGAATTATTTATACTCTCTCTG
986
P1-82_t7    < GAGTGGTGCATCAATAAGACAAATCGCAGAGTATTTCCTGAATTATTTATACTCTCTCTG
999
P7-82_t7    < GAGTGGTGCATCAATAAGACAAATCGCAGAGTATTTCCTGAATTATTTATACTCTCCCTG
1003
P6-82_t7    < GAGTGGTGCATCAATAAGACAAATCGCAGAGTATTTCCTGAATTATTTATACTCTCCCTG
1014
P4-82_t7    < GAGTGGTGCATCAATAAGACAAATCGCAGAGTATTTCCTGAATTATTTATACTCTCTCTG
1031
P2-82_t7    < GAGTGGTGCATCAATAAGACAAATCGCAGAGTATTTCCTGAATTATTTATACTCTCTCTG
1044
CONSENSUS   > GAGTGGTGCATCAATAAGACAAATCGCAGAGTATTTCCTGAATTATTTATACTCTCyCTG
1380
              .........+.........+.........+.........+.........+.........+
P9-82_t7    < TTAGTTTATATTGAATATACTGGGTTTATATGGTGGTTTCATACAAACTTAGCTGATGAT
804
P5-82_t7    < TTAGTTTATATTGAATATACTGGGTTTATATGGTGGCTTCATACAAACTTAGCTGATGAT
1017
P10-82_t7   < TTAGTTTATATTGAATATACTGGGTTTATATGGTGGTTTCATACAAACTTAGCTGATGAT
1024
P8-82_t7    < TTAGTTTATATTGAATATACTGGGTTTATATGGTGGTTTCATACAAACTTAGCTGATGAT
1028
P3-82_t7    < TTAGTTTATATTGAATATACTGGGTTTATATGGTGGTTTCATACAAACTTAGCTGATGAT
1046
P1-82_t7    < TTAGTTTATATTGAATATACTGGGTTTATATGGTGGTTTCATACAAACTTAGCTGATGAT
1059
P7-82_t7    < TTAGTTTATATTGAATATACTGGGTTTATATGGTGGTTTCATACAAACTTAGCTGATGAT
1063
P6-82_t7    < TTAGTTTATATTGAATATACTGGGTTTATATGGTGGTTTCATACAAACTTAGCTGATGAT
1074
P4-82_t7    < TTAGTTTATATTGAATATACTGGGTTTATATGGTGGTTTCATACAAACTTAGCTGATGAT
1091
P2-82_t7    < TTAGTTTATATTGAATATACTGGGTTTATATGGTGGTTTCATACAAACTTAGCTGATGAT
1104
CONSENSUS   > TTAGTTTATATTGAATATACTGGGTTTATATGGTGGtTTCATACAAACTTAGCTGATGAT
1440
              .........+.........+.........+.........+.........+.........+
P9-82_t7    < TATTTAAAATCCTTTCCCTACTCTTTCTGAGTTATAGAAATATTTTTCTTTCCCTCTGAG
864
P5-82_t7    < TATTTAAAATCCTTTCCCTACTCTTTCTGAGTTATAGAAATATTTTTCTTTCCCTCTGAG
1077
P10-82_t7   < TATTTAAAATCCTTTCCCTACTCTTTCTGAGTTATAGAAATATTTTTCTTTCCCTCTGAG
1084
P8-82_t7    < TATTTAAAATCCTTTCCCTACTCTTTCTGAGTTATAGAAATATTTTTCTTTCCCTCTGAG
1088
P3-82_t7    < TATTTAAAATCCTTTCCCTACTCTTTCTGAGTTATAGAAATATTTTTCCTTCCCTCTGAG
1106
```

FIGURE 1 CONTINUED

```
P1-82_t7   < TATTTAAAATCCTTTCCCTACTCTTTCTGAGTTATAGAAATATTTTTCTTTCCCTCTGAG
1119
P7-82_t7   < TATTTAAAATCCTTTCCCTACTCTTTCTGAGTTATAGAAATATTTTTCTTTCCCTCTGAG
1123
P6-82_t7   < TATTTAAAATCCTTTCCCTACTCTTTCTGAGTTATAGAAATATTTTTCTTTCCCTCTGAG
1134
P4-82_t7   < TATTTAAAATCCTTTCCCTACTCTTTCTGAGTTATAGAAATATTTTTCTTTCCCTCTGAG
1151
P2-82_t7   < TATTTAAAATCCTTTCCCTACTCTTTCTGAGTTATAGAAATATTTTTCTTTCCCTCTGAG
1164
CONSENSUS  > TATTTAAAATCCTTTCCCTACTCTTTCTGAGTTATAGAAATATTTTTCtTTCCCTCTGAG
1500
              .........+.........+.........+.........+.........+.........+

P9-82_t7   < AATAAAATTTCAAGTGAATTCCTGCAGCCCGGGGATCCACTAGTTCTAGAGCG
917
P5-82_t7   < AATAAAATTTCAAGTGANKTCCTGCAGCCCGGGGATCCACTAGTTCTAGAGCG
1130
P10-82_t7  < AATAAAATTTCAAGTGAATTCCTGCAGCCCGGGGATCCACTAGTTCTAGAGCG
1137
P8-82_t7   < AATAAAATTTCAAGTGAATTCCTGCAGCCCGGGGATCCACTAGTTCTAGAGCG
1141
P3-82_t7   < AATAAAATTTCAAGTGANKTCCTGCAGCCCGGGGATCCACTAGTTCTAG
1155
P1-82_t7   < AATAAAATTTCAAGTGAATTCCTGCAGCCCGGGGATCCACTAGTTCTAGA
1169
P7-82_t7   < AATAAAATTTCAAGTGAATTCCTGCAGCCCGGGGATCCACTAGTTCTAGAGC
1175
P6-82_t7   < AATAAAATTTCAAGTGAATTCCTGCAGCCCGGGGATCCACTAGTTCTAGAGC
1186
P4-82_t7   < AATAAAATTTCAAGTGAATTCCTGCAGCCCGGGGATCCACTAGTTCTAG
1200
P2-82_t7   < AATAAAATTTCAAGTGAATTCCTGCAGCCCGGGGATCCACTAGTTCTAGAGCG
1217
CONSENSUS  > AATAAAATTTCAAGTGaattCCTGCAGCCCGGGGATCCACTAGTTCTAGAGCG
1553
              .........+.........+.........+.........+.........+.........+
```

ANIMAL GENOTYPING METHOD

This invention relates to a method for identifying a physical trait of an animal by genotyping in the region of a gene which determines variation in the physical trait and determining whether the animal possesses a specific variant of a gene by reference to the DNA in the region of the gene, rather than by genotyping for the gene itself. In particular, the invention relates to a method for determining whether a bovine animal possesses a gene for the β-casein $A^1$ protein or a gene for the β-casein $A^2$ protein and therefore the ability of bovine cows to produce β-casein $A^1$ or β-casein $A^2$ in their milk.

BACKGROUND

Consumers demand high quality and low price when purchasing goods such as dairy and meat products. However, many consumers also want assurance that the products and production systems are managed to minimise risk and maximise benefits to human health, while also being non-detrimental to the environment and to the welfare of animals.

It is well known that the genetics of an animal has a substantial impact on production and product quality, and on health, environmental and animal welfare issues. The ability to determine a phenotype of an animal by using a genetic test is a valuable tool for achieving rapid identification of animals and animal products with beneficial characteristics and for forming a group of animals having enhanced production and/or product quality. Animals can be grouped based on genetic differences that relate to animal or animal product traits that are of economic interest. In the case of the dairy industry, examples of important traits are milk production, milk protein content, fat production, and specific components of milk that are associated with health, for example the absence of the β-casein $A^1$ protein or the percentage of saturated fats.

In a typical genetic test, the DNA sequence of a gene encoding a protein or group of proteins related to a physical trait of interest will be known. A DNA sample is obtained from an animal and a combination of polymerase chain reaction (PCR) amplification, DNA fragment analysis, and data processing is used to identify the DNA present at the known location for the gene in the animal's genome. Highly automated testing enables the presence of a gene or gene variant, and therefore the ability to exhibit a physical trait, to be determined for a large number of animals comparatively quickly and efficiently.

The gene that is responsible for a particular physical trait of an animal may be identifiable by a single nucleotide polymorphism (SNP). An SNP is a DNA sequence at a location in an animal's genome which is different to the DNA sequence at the same location in the genome of another animal by virtue of only one nucleotide. Even a difference as small as this can mean an animal exhibits a particular physical trait whereas another animal does not.

One example of the significance of an SNP is the genetic makeup of a bovine cow that enables the production of β-casein proteins in its milk. Typically, a cow will produce β-caseins in its milk. However, several β-casein variants are known including $A^1$, $A^2$, $A^3$, B, C, D, E, and F. One difference between the $A^2$, $A^3$, D, E, and F variants on the one hand and the $A^1$, B, and C variants on the other hand is that the former group has a proline residue at position 67 of the β-casein protein whereas the latter group has a histidine residue at position 67. This difference is determined by substitution of the nucleotide adenine with the nucleotide cytosine at position 200 of the coding region of the β-casein gene. It is therefore possible to distinguish between the two groups of β-casein variants by identifying and testing for the SNP that encodes for the β-casein protein of an animal.

There are a number of reports indicating that the presence of β-casein $A^1$ in the human diet is linked with the incidence of certain diseases, specifically diabetes (Elliott, R. B., Harris, D. P., Hill, J. P., Bibby, N. J., Wasmuth, H. E., Type I (Insulin-Dependent) Diabetes Mellitus and Cow Milk: Casein Variant Consumption, Diabetologia 1999; 42:292-6; Wasmuth, H. E., Rosenbauer, J., Elliot, R. B., McLachlan, C., Erhardt, G., Giani, G., Kolb, H., β-Casein A1 Consumption and Incidence of Type 1 Diabetes in Germany. Kongress der Europäischen Diabetesgesellschaft vom 28.-30. Sep. 1999 in Brüssels/Belgium. Proceedings published in Diabetologia 42 (Suppl. 1): A88; 1999) and coronary heart disease (McLachlan, C. N. (2001) β-casein A1, Ischaemic Heart Disease Mortality, and Other Illnesses. *Med. Hypotheses* 56(2): 262-72).

In addition to phenotyping a cow by identifying the particular β-casein variant or variants produced in the cow's milk, it is well known to genotype a cow by identifying the SNP it possesses to gain knowledge of whether the cow has the ability to produce a certain β-casein variant. A method of selecting bovine cows on the basis of such genotyping to form milking herds which will produce milk free of the β-casein $A^1$ variant, and preferably solely the β-casein $A^2$ variant, is described in PCT/NZ96/00039 (published as WO 96/36239).

Studies have shown that SNPs, or other DNA variants (tandem repeats, insertion-deletions) are valuable in predicting a disease, the quality of an animal product, or a production benefit. However, in cases where genetic selection is used to sort, cull or mate animals, a selection strategy based on the use of a single SNP or trait is sub-optimal. This is because an SNP, such as an SNP within the β-casein gene, is not randomly associated with the surrounding DNA. The region of DNA that surrounds the genotyped SNP may encode one or more functions which also influence a physical trait. Selection based on a single SNP may therefore inadvertently select for traits additional to the trait of interest.

The inventors have now found that it is possible to determine whether a bovine animal possesses a gene for the β-casein $A^1$ protein or a gene for the β-casein $A^2$ protein, not by identifying the DNA of that gene, but by identifying SNPs or haplotypes (combinations of SNPs) in the region of the animal's genome where the gene for β-casein is located.

It is therefore an object of the invention to provide a novel method of genotyping an animal for its β-casein gene, or to at least provide a useful alternative to known methods.

STATEMENTS OF INVENTION

In a first aspect of the invention there is provided a method for determining whether a bovine animal possesses a gene encoding for the protein β-casein $A^1$ or a gene encoding for the protein β-casein $A^2$ by testing the DNA of the animal for the presence of at least one DNA marker for either of the genes, but not for the presence of a DNA marker in either of the genes.

In a preferred embodiment of the invention each of the at least one DNA markers represents a single nucleotide polymorphism (SNP), a tandem repeat, or an insertion-deletion. Preferably the at least one DNA markers represents an SNP.

Although the method may be used to determine the β-casein genotype for bovine bulls or cows, the bovine animal of the invention is preferably a cow.

The physical trait of the animal may be any trait which affects the quality or volume of a product produced from the animal, or may relate to a disease or disorder of the animal, or to the avoidance of a disease or disorder. Preferably the trait relates to the production of milk from a bovine cow, including the amount or composition of milk proteins or milk fat. The one or more physical traits include, but are not limited to, β- or κ-casein variant content, whey content, protein content, fat content, fatty acid profile, conjugated linoleic acid content, β-lactoglobulin content, lactoferrin content, somatic cell count, daily milk yield, fat yield, protein yield, and full-lactation yields of milk, fat and protein.

In a further preferred embodiment of the invention the physical trait is the presence or absence of β-casein $A^2$ in the milk of a bovine cow. In an alternative embodiment, the physical trait is the presence or absence of β-casein $A^1$ in the milk of the cow.

In a preferred embodiment of the invention the at least one DNA marker is a marker for the gene encoding for β-casein $A^1$. In an alternative embodiment of the invention the at least one DNA marker is a marker for the gene encoding for β-casein $A^2$.

The DNA of the animal tested may be obtained from any tissue of the animal which contains or contained nucleated cells, preferably blood, sperm, hair, or milk of the animal.

Preferably the SNPs are derived from chromosome 6 of a Bos taurus bovine animal. In a preferred embodiment the at least one DNA marker is a group of 8 SNPs in the region of the gene for the β-casein protein in a bovine animal.

In a second aspect of the invention there is provided a method of producing milk substantially free of β-casein $A^1$ including the steps:
  a) determining whether one or more bovine cows possesses a gene encoding for the protein β-casein $A^1$ or a gene encoding for the protein β-casein $A^2$ according to the first aspect of the invention;
  b) selecting those cows that do not have a gene encoding for the protein β-casein $A^1$; and
  c) milking the selected cows.

Preferably the milk produced by this method is milk containing β-casein which is substantially all β-casein $A^2$.

In another aspect of the invention there is provided a method of forming a herd of bovine cows by testing the DNA of each cow in accordance with the method of the first aspect of the invention and selecting those cows that possess a gene encoding for β-casein $A^2$ and do not possess a gene encoding for β-casein $A^1$.

In another aspect there is provided milk obtained from a bovine cow that has been tested in accordance with the method of the first aspect of the invention.

In a further aspect of the invention there is provided a food or food product containing, or processed from, the milk of this invention.

In yet another aspect of the invention there is provided semen or an embryo from an animal that has or have been tested in accordance with the method of this invention. Preferably the semen or embryo is used for producing offspring using any artificial reproduction technique.

BRIEF DESCRIPTION OF THE DRAWINGS

FIG. 1 is the output from the program Gelassemble showing the alignment of sequences corresponding to plasmids containing inserts derived from the αS2 genes of 5 pooled DNAs from $A^1$ homozygous cattle and from 5 $A^2$ homozygous cattle bi-directionally sequenced from the t7 and t3 primer sites in the pbluescript plasmid. The sequences derived from $A^1$ homozygous cattle are SEQ ID NO: 35, SEQ ID NO: 40, SEQ ID NO: 39, SEQ ID NO: 38, and SEQ ID NO: 32, corresponding to output P1 to P5-82_t3, respectively, and SEQ ID NO: 46, SEQ ID NO: 50, SEQ ID NO: 45, SEQ ID NO: 49, and SEQ ID NO: 42, corresponding to output P1 to P5-82_t7, respectively. The sequences derived $A^2$ homozygous cattle SEQ ID NO: 31, SEQ ID NO: 33, SEQ ID NO: 36, SEQ ID NO: 34, and SEQ ID NO: 37, corresponding to output P6 to P10-82_t3, respectively, and SEQ ID NO: 48, SEQ ID NO: 47, SEQ ID NO: 44, SEQ ID NO: 41, and SEQ ID NO: 43, corresponding to output P6 to P10_t7. A consensus sequence is also shown, SEQ ID NO: 51, which corresponds to output CONSENSUS.

DETAILED DESCRIPTION

This invention enables a user to group a population of cattle, or tissue derived from an animal (such as blood, sperm, hair, or milk) based on genetic differences. In a preferred embodiment of the invention these genetic differences are SNPs or combinations of SNPs. The use of such SNPs, as well as enabling a user to catalogue populations of animals, can also be used to predict an animal phenotype.

Examples of traits relating to milk production include milk yield, milk protein composition, amount of milk fat, and more specific traits such as the presence of β-casein variants, the proportion of saturated and unsaturated fat, and the number of somatic cells present in the milk.

The variant caseins are distinguished by a small number of amino acid changes in the overall sequence of these proteins. In bovine cattle, the difference between the $A^2$ and $A^1$ variant of β-casein is a single change in amino acid from a proline to histidine at position 67 of this protein. The relevant SNPs occur on chromosome 6 of Bos taurus bovines.

While other β-casein variants have histidine as opposed to proline at position 67, they are usually minor variants and for the purposes of describing this invention are to be considered generally as β-casein $A^1$. Similarly, those β-casein variants, in addition to β-casein $A^2$, which have proline at position 67 are usually minor variants and are to be considered generally as β-casein $A^2$.

A determination can be made as to whether cattle, or tissue derived from cattle, possesses genes that code exclusively for the $A^1$ variant of β-casein ($A^1$ homozygous), exclusively for the $A^2$ variant ($A^2$ homozygous), or for a mixture of the $A^1$ and $A^2$ variants ($A^1/A^2$ heterozygous). This allows cattle to be identified which produce milk containing solely β-casein $A^1$, solely β-casein $A^2$, or a mixture of both of these casein variants. It also allows cattle to be identified which may produce offspring with the ability to produce milk containing solely β-casein $A^1$, solely β-casein $A^2$, or a mixture of both of these casein variants.

In this way, herds of milking cows can be formed which produce milk having a particular physical trait, for example the absence of the β-casein $A^1$ protein or the presence of only β-casein $A^2$ of the β-casein variants.

An additional feature of the invention is that once animals with a particular genotype or haplotype have been selected and milk is produced from them, the origin of the milk, or other products such as milk powder and processed milk products, can be verified as being produced from the selected animals. This has the benefit of providing consumers with confidence that the milk is indeed from animals of the desired genotype or haplotype group.

Specifically, the inventors have shown that SNPs can be readily identified in regions outside the β-casein gene which are predictive of β-casein protein type. These SNPs are therefore also predictive, or potentially causative or partially causative, of health risks associated with β-casein alleles. A population of cattle with eight SNPs has been identified and analysed. The SNPs are derived from the casein gene cluster of cattle which includes the gene encoding β-casein. This region of DNA is estimated to consist of about 200-300 kilobases of DNA. Of these eight SNPs associated randomly in different individuals, a theoretical number of possible combinations (or haplotypes) of 2 to the power of eight ($2^8$) would be expected. Surprisingly, the number of haplotypes observed with these SNPs and subsets of these SNPs is much less than what would be expected randomly. It is therefore possible, using the discovery of the specific associations between the SNPs, to correctly class a cattle population into haplotype groups using only a small number of SNPs. More importantly, these haplotypes can be used to predict specific phenotypes in individuals or populations, such as the identity of the α-S1, α-S2, β-, and κ-casein milk protein variants.

The associations between SNP haplotype(s) and production and product quality traits were examined. These traits, specific to bovine milk, include characteristics associated with β- or κ-casein variants, whey %, protein %, fat %, fatty acid profiles (C4 to C22), conjugated linoleic acid content (CLA), melting point, β-lactoglobulin content, lactoferrin content, somatic cell count, daily milk yield, fat yield, protein yield, full-lactation yields of milk, fat and protein.

It was found that significant associations exist between casein region haplotype and production and product quality traits, such as somatic cell count, fat %, protein %, β-casein yield, and fatty acid profile.

Information about the non-random association between adjacent DNA markers and combinations of these markers (i.e. haplotypes) in a population, and the relationship between those markers and haplotypes and physical traits has the following potential benefits:

1. Selection procedures for selecting animals based on a single marker can be modified to avoid or minimise the inadvertent amplification of undesirable physical traits, which may result from co-selection of linked genetic information with known or unknown effects on phenotype.
2. Identification of specific combinations of SNP alleles within a region of the genome (haplotypes) which provide an equal or better predictor of product quality than any single SNP within the region.
3. Identification of a subset of SNP alleles which efficiently predict variation in a larger group of known or unknown SNPs.
4. Prediction, with a useful degree of accuracy, of the identity of an SNP which for any reason cannot itself be genotyped.
5. Identification of the major association groups occurring within a region of a genome into which new, as yet undiscovered, DNA variations in that region will typically fall.

This invention enables the identification of SNPs, and the use of SNPs and SNP haplotypes to:

1. Provide the means to efficiently select, sort or group animals producing specific α-casein and/or β-casein and/or κ-casein variants using a minimum of SNP tests. In particular, genotypes and phenotypes related to casein variants can be inferred by genotyping a small number of associated SNPs. The use of associated markers that are linked to multiple genotypes or phenotypes, or to genotypes that are unable to be tested, can provide economic and technological advantages.
2. Predict the performance of dairy cattle and therefore product quality and heath effects of the milk from the cattle, or the progeny of the cattle, as well as or better than any single SNP from the casein region.
3. Catalogue much of the variation in the casein genes in the cattle population with a minimum number of markers therefore providing an efficient means to class or group cattle according to predicted performance or product quality.
4. Provide an efficient means of selecting specific casein types (e.g. β-casein $A^2$) while minimising the alteration of the frequency of variants in related caseins.
5. Provide a means to select for other casein genes or associated traits, while at the same time increasing the proportion of β-casein $A^2$ animals in a specific herd.

The invention is described in further detail by reference to the following examples that demonstrate the procedure for discovering SNPs and how these can be used. It is to be appreciated that these examples do not limit the scope of this invention. Any person skilled in this area of technology will recognise that these procedures may be used generally to discover useful SNPs in the genome of an animal.

EXAMPLES

Example 1

Identification of SNPs in a Population

The DNA sequences in the αs1, αs2 and β-casein genes from a number of individual cattle were determined and analysed to identify SNPs. A comparison of these sequences enabled the identification of polymorphic sequences.

The oligonucleotide primers SEQ ID NO:1 to SEQ ID NO:14 were designed and synthesised. The sequences are based on the published sequences of the Bos taurus αs1 (ACCESSION X59856) and αs2 (ACCESSION M94327) sequences. Each primer pair was also designed so that any resulting PCR product would have an Xho1 and EcoR1 restriction endonuclease site at its flanking ends. The conditions for PCR amplification were optimised for the appropriate primer pairs:

SEQ ID NO:1, SEQ ID NO:2
SEQ ID NO:3, SEQ ID NO:4
SEQ ID NO:5, SEQ ID NO:6
SEQ ID NO:7, SEQ ID NO:8
SEQ ID NO:9, SEQ ID NO:10
SEQ ID NO:11, SEQ ID NO:12
SEQ ID NO:13, SEQ ID NO:14

From these results it was determined that regions of DNA corresponding to exons 1-2 and exons 3-6 of the αs1 gene and exons 1-2 and 17-18 of the αs2 gene gave PCR products of the anticipated sizes.

Seminal genomic DNA was purified from cattle that were previously genotyped and shown to be either carriers of the $A^1$ or $A^2$ variant of the β-casein protein. DNA was amplified using genomic DNA mixed in equimolar concentrations from five $A^1$ homozygous ($A^1$ DNA) and five $A^2$ ($A^2$ DNA) homozygous animals. The PCR products of amplification from $A^1$ DNA and $A^2$ DNA were purified with a High Pure PCR Product Purification Kit, digested with EcoR1 and Xho1 restriction endonucleases, and the enzymes then heat inactivated by heating for 20 min at 70° C. A portion of each of these samples was ligated into the plasmid pBluescript KS (Stratagene) that was previously digested with Xho1 and EcoR1 restriction enzyme, treated with shrimp alkaline phosphatase (Amersham Pharmacia Biotech Inc.) and finally heat inactivated for 20 min at 70° C.

The ligated plasmids were used to transform chemically competent E. coli strain XL1-Blue. Individual colonies containing either inserts from derived from $A^1$ or $A^2$ DNA were analysed by colony PCR. For the αs1 gene region, plasmids containing DNA from exons 3-6 (3 each from the $A^1$ and $A^2$ DNA) and exons 1-2 (5 derived from $A^1$ DNA and 5 from $A^2$ DNA) were sequenced. In the αs2 region plasmids from the region spanning exon 1-2 (5 each from the $A^1$ and $A^2$ DNA) and exon 17-18 (5 each from the $A^1$ and $A^2$ DNA) were sequenced. A comparison of these sequences enabled identification of polymorphic sequences and nucleotides. Examples of such polymorphic sequences are given in SEQ. ID. NOs:15-28.

Example 2

The Use of SNPs as Predictive Tools

The sequences were analysed by alignment using programs from the *Wisconsin Package Version* 10.2, *Genetics Computer Group* (*GCG*), Madison, Wis. Surprisingly, the analyses revealed that a number of the SNPs could be readily used to distinguish an $A^1$ animal from an $A^2$ animal. The alignment of the sequences derived from the αs2 genes of $A^1$ homozygous and $A^2$ homozygous animals revealed that a number of SNPs in these sequences were linked directly with either the $A^1$ or the $A^2$ animal. Therefore, as shown in FIG. 1, a total of 10 plasmids containing inserts derived from the αS2 genes of 5 pooled DNAs from $A^1$ animals and from 5 $A^2$ animals were sequenced bi-directionally from the t7 and t3 primer sites in the pbluescript plasmid.

The sequences were all aligned using the programs Gelstart, Gelenter, Gelmerge and Gelassemble. The output from Gelassemble is given in FIG. 1 where the sequences from P1 to P5-82_t3 or t7 are derived from $A^1$ homozygous cattle and the sequences P6 to P10-82_t3 or t7 are from $A^2$ homozygous cattle. A consensus sequence is also given in this alignment. Multiple differences or polymorphisms occur between the sequences from different individuals. Many of these differences are single deletions or are single nucleotide base differences (SNPs) occurring between individuals. In the sequences three SNPs at positions 664, 926 and 1377, reading consecutively from the first base of the consensus sequence, have a guanine (G), thymine (T) and T respectively in only the $A^1$ animal sequences. Conversely, in the $A^2$ animal sequences an adenine (A), G, and cytosine (C) occur respectively at these positions of the sequence. The three SNPs at positions 664, 926 and 1377 are shown in bold and are underlined. The EcoR1 (GAATTC) and Xho1 (CTCGAG) restriction endonuclease recognition site are also shown in bold.

The identity of these nucleotides can also be determined by methods other than by sequencing, especially those methods used in combination with genomic sequence-specific amplification technologies, such as the polymerase chain reaction (Mullis, K. et al., Cold Spring Harbor Symp. Quant. Biol. 51:263-273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194)). Examples of such methods include an exonuclease resistance method (U.S. Pat. No. 4,656,127), primer-guided nucleotide incorporation procedures for assaying polymorphic sites in DNA (Komher, J. S. et al., Nucl. Acids. Res. 17:7779-7784 (1989); Sokolov, B. P., Nucl. Acids Res. 18:3671 (1990); Syvanen, A.-C., et al., Genomics 8:684-692 (1990); Kuppuswamy, M. N. et al., Proc. Natl. Acad. Sci. (U.S.A.) 88:1143-1147 (1991); Prezant, T. R. et al., Hum. Mutat. 1:159-164 (1992); Ugozzoli, L. et al., GATA 9:107-112 (1992); Nyren, P. et al., Anal. Biochem. 208:171-175 (1993)), the "Oligonucleotide Ligation Assay" ("OLA") (Landegren, U. et al., Science 241: 1077-1080 (1988)), pyrosequencing (Kittles et al. Cancer Epidemiol Biomarkers Prev 2001 September; 10(9):943-7), and MassARRAY (Sequenom Corp.).

Example 3

The Use of SNPs to Predict a Genotype or Phenotype by Using an Alternative Genotyping Method This example shows that the identity of SNPs, in a larger population than used in Example 2, can be determined with methods other than DNA sequencing and that these SNPs can be used to predict a genotype or phenotype. Specifically, a method based on PCR amplification, primer extension and finally analysis of the primer extension product with a Sequenom Mass Spectroscopy apparatus was used to predict whether an animal, or tissue derived from an animal, contains either one or two copies of the gene encoding the $A^1$ (or conversely the $A^2$) variant of the milk β-casein gene.

The semen from a known heterozygous $A^1A^2$ animal was used to artificially inseminate cows. DNA samples (from milk) were isolated from the sire and from the progeny of these matings. The identity of the progeny with respect to them being phenotypically or genotypically $A^1$ or $A^2$ was determined independently. A total of 71 progeny were analysed for SNPs associated with AC00069, AC00070, AC00055, AC00057, AC00058, AC00059, AC00060, AC00061, AC00063, and AC00064 (see SEQ ID. listing) with a standard procedure from Sequenom Inc. In addition to these SNPs, markers AC000069 and AC000070, that determine the identity of the milk protein variant β-casein A or B, were also genotyped.

The genotypes from individuals with complete genotypes were analysed to derive their haplotypes (i.e. the combination and organisation of the markers as they occur physically their chromosomes). Initially, the package Crimap was used to check the SNPs for anomalies whereupon the maternal and two paternal haplotypes were derived with the program Simwalk. The haplotypes derived from analyses of these SNPs, including the SNP determining the $A^1$ or $A^2$, β-casein milk phenotype, are given in Table 1.

TABLE 1

| animal | Derived haplotypes of cattle individuals | | | | | | | | | | |
|---|---|---|---|---|---|---|---|---|---|---|---|
| | haplolype | | | | | | | | | | |
| ID | ac69 | ac70 | ac55 | ac57 | A1 or 2 | ac58 | ac59 | ac60 | ac61 | ac63 | ac64 |
| 87203a | C | A | C | C | A1 | C | G | T | G | T | T |
| 87203b | C | A | T | T | A2 | C | A | C | A | G | C |
| 5001 | T | C | C | T | A1 | T | G | T | A | T | C |

TABLE 1-continued

Derived haplotypes of cattle individuals

| animal ID | ac69 | ac70 | ac55 | ac57 | A1 or 2 | ac58 | ac59 | ac60 | ac61 | ac63 | ac64 |
|---|---|---|---|---|---|---|---|---|---|---|---|
| 5002 | T | C | C | T | A2 | T | G | C | A | G | C |
| 5003 | C | A | C | T | A2 | T | A | T | A | T | C |
| 5004 | C | A | T | T | A2 | T | G | C | A | G | C |
| 5005 | T | C | C | T | A2 | T | G | C | A | G | C |
| 5006 | C | A | C | T | A1 | T | A | T | G | T | T |
| 5019 | C | A | T | T | A1 | C | G | T | G | T | T |
| 5022 | C | A | C | T | A1 | T | A | T | G | T | T |
| 5023 | C | A | T | C | A2 | C | G | C | A | G | C |
| 5025 | T | C | C | T | A2 | C | A | C | A | G | C |
| 5027 | C | A | C | T | A1 | T | G | T | G | T | T |
| 5029 | C | A | C | C | A1 | T | G | T | G | T | T |
| 5032 | C | A | T | T | A2 | C | A | C | A | G | C |
| 5034 | C | A | T | T | A2 | T | A | C | A | G | C |
| 5035 | C | A | C | T | A1 | T | A | T | G | T | T |
| 5036 | T | C | T | T | A2 | T | A | T | A | T | C |
| 5037 | C | A | C | C | A1 | T | G | T | G | T | T |
| 5038 | T | C | C | T | A2 | C | A | C | A | G | C |
| 5040 | T | C | C | C | A2 | T | G | C | A | G | C |
| 5044 | T | C | C | T | A2 | T | G | C | A | G | C |
| 5045 | T | C | T | T | A2 | T | G | C | A | G | C |
| 5048 | C | A | T | T | A1 | T | G | T | G | T | C |
| 5049 | C | A | C | T | A1 | C | G | T | G | T | T |
| 5050 | T | C | C | T | A1 | T | G | T | G | T | T |
| 5053 | C | A | T | T | A2 | T | G | C | A | G | C |
| 5054 | C | A | C | T | A1 | T | G | T | G | T | T |
| 5055 | C | A | C | T | A1 | T | G | T | G | T | T |
| 5056 | C | A | T | T | A2 | T | A | C | A | G | C |
| 5057 | C | A | T | T | A2 | T | A | C | A | G | C |
| 5061 | C | A | C | T | A1 | T | G | C | G | T | T |
| 5062 | C | A | C | T | A1 | T | G | T | G | T | T |
| 5064 | C | A | C | T | A2 | T | A | T | A | T | C |
| 5065 | T | C | C | T | A1 | T | G | T | G | T | T |
| 5066 | C | A | C | T | A1 | C | G | T | G | T | T |
| 5069 | C | A | C | T | A1 | C | G | T | G | T | T |
| 5070 | C | A | T | T | A2 | C | G | C | A | G | C |

There are a total of 38 haplotypes derived that consist two paternal and 36 maternal haplotypes. However, with closer observation there are only 18 unique haplotypes associated with these animals. More importantly these SNPS, or more specifically a small subset of these SNPs, can be used to discriminate between animals having the $A^1$ or $A^2$ genotypes. This study showed that in the 36 animals and the sire it would require the genotyping of only one of the SNPs (AC00061) to infer successfully all but one of the identities of these animals (i.e. 97% accuracy). The genotyping of a further two SNPs (AC00059 and AC00063) allows all the animals in this population to be successfully identified in terms of being of $A^1$ or $A^2$ genotype and phenotype (see Table 2).

TABLE 2

Prediction of β-casein genotype with a haplotype of markers outside the β-casein gene

| Haplotype of markers outside β-casein gene | | | β-casein nucleotide 200 (A1/A2) | |
|---|---|---|---|---|
| AC61 | AC59 | AC63 | nC (A2) | nA (A1) |
| A | A | G | 7 | |
| A | A | T | 3 | |
| A | G | G | 9 | |
| A | G | T | | 1 |
| G | A | G | | 3 |
| G | G | T | | 15 |

Although the invention has been described by way of example, it should be appreciated that variations and modifications may be made without departing from the scope of the invention. Furthermore, where known equivalents exist to specific features, such equivalents are incorporated as if specifically referred to in this specification.

The invention claimed is:

1. A method for determining whether a bovine animal possesses a gene encoding for the protein β-casein $A^1$ or a gene encoding for the protein β-casein $A^2$ by testing the DNA of the animal for the presence of at least one DNA marker for either of the β-casein $A^1$ or β-casein $A^2$ genes, where the at least one DNA marker is located in a gene encoding for the protein $α_{s2}$-casein.

2. The method as claimed in claim 1, where the at least one DNA marker is located in exon 17 or exon 18 of the $α_{s2}$-casein gene.

3. The method as claimed in claim 1, where each of the at least one DNA marker is an SNP.

4. The method as claimed in claim 3, where the SNP is SEQ ID No:21.

5. The method as claimed in claim 4 which further comprises testing for the presence of the SNPs of SEQ ID No:19 and SEQ ID No:23.

6. The method as claimed in claim 5 where the bovine animal is a cow.

7. The method as claimed in claim 6, where the presence of the at least one DNA marker is linked with the presence or absence of β-casein $A^1$ in milk produced by the cow.

8. The method as claimed in claim 6, where the presence of the at least one DNA marker is linked with the presence or absence of β-casein $A^2$ in milk produced by the cow.

9. The method as claimed in claim 1, where the at least one DNA marker is a marker for the gene encoding for β-casein $A^1$.

10. The method as claimed in claim 1, where the at least one DNA marker is a marker for the gene encoding for β-casein $A^2$.

11. The method as claimed in claim 1, where the DNA of the bovine animal is obtained from any tissue of the bovine animal which contains or contained nucleated cells.

12. The method as claimed in claim 11, where the DNA of the animal is obtained from blood, sperm, hair, or milk of the animal.

13. A method of producing milk substantially free of β-casein $A^1$ including the steps:
   determining whether one or more bovine cows possesses a gene encoding for the protein β-casein $A^1$ or a gene encoding for the protein β-casein $A^2$ according to the method of claim 1;
   selecting those cows that do not have a gene encoding for the protein β-casein $A^1$; and
   milking the selected cows.

14. The method as claimed in claim 13, where the milk contains β-casein which is substantially all β-casein $A^2$.

15. A method of forming a herd of bovine cows by testing the DNA of each cow in accordance with the method of claim 1 and selecting those cows that possess a gene encoding for β-casein $A^2$ and do not possess a gene encoding for β-casein $A^1$.

* * * * *

UNITED STATES PATENT AND TRADEMARK OFFICE
CERTIFICATE OF CORRECTION

PATENT NO. : 7,629,119 B2 Page 1 of 1
APPLICATION NO. : 10/515940
DATED : December 8, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1027 days.

Signed and Sealed this

Second Day of November, 2010

David J. Kappos
*Director of the United States Patent and Trademark Office*

```
                            SEQUENCE LISTING

<160> NUMBER OF SEQ IDS NOS: 51

<210> SEQ ID NO 1
<211> LENGTH: 28
<212> TYPE: DNA
<213> ORGANISM: Bos taurus

<400> SEQUENCE: 1
tgcctcgagt acttgtcttc cttttagg                                          28

<210> SEQ ID NO 2
<211> LENGTH: 25
<212> TYPE: DNA
<213> ORGANISM: Bos taurus

<400> SEQUENCE: 2
cttgaattct ttgcaagggc aacag                                             25

<210> SEQ ID NO 3
<211> LENGTH: 23
<212> TYPE: DNA
<213> ORGANISM: Bos taurus

<400> SEQUENCE: 3
aaggaattcg taaggaacgc aaa                                               23

<210> SEQ ID NO 4
<211> LENGTH: 24
<212> TYPE: DNA
<213> ORGANISM: Bos taurus

<400> SEQUENCE: 4
tcactcgagg agagctgctc tctg                                              24

<210> SEQ ID NO 5
<211> LENGTH: 25
<212> TYPE: DNA
<213> ORGANISM: Bos taurus

<400> SEQUENCE: 5
tgactcgaga agaaaagaat cgcct                                             25

<210> SEQ ID NO 6
<211> LENGTH: 23
<212> TYPE: DNA
<213> ORGANISM: Bos taurus

<400> SEQUENCE: 6
agtgaattcc agaatcttaa agg                                               23

<210> SEQ ID NO 7
<211> LENGTH: 27
<212> TYPE: DNA
<213> ORGANISM: Bos taurus

<400> SEQUENCE: 7
agactcgagc acagatttcc agttcta                                           27
```

```
<210> SEQ ID NO 8
<211> LENGTH: 29
<212> TYPE: DNA
<213> ORGANISM: Bos taurus

<400> SEQUENCE: 8
aaagaattca cttgaaattt tattctcag                               29

<210> SEQ ID NO 9
<211> LENGTH: 24
<212> TYPE: DNA
<213> ORGANISM: Bos taurus

<400> SEQUENCE: 9
tcacctcgag catcaaccca gctt                                    24

<210> SEQ ID NO 10
<211> LENGTH: 26
<212> TYPE: DNA
<213> ORGANISM: Bos taurus

<400> SEQUENCE: 10
gatgagaatt ctcatggttg tcaaga                                  26

<210> SEQ ID NO 11
<211> LENGTH: 24
<212> TYPE: DNA
<213> ORGANISM: Bos taurus

<400> SEQUENCE: 11
atcctctcga gcaccaagga ctcc                                    24

<210> SEQ ID NO 12
<211> LENGTH: 26
<212> TYPE: DNA
<213> ORGANISM: Bos taurus

<400> SEQUENCE: 12
tgctgaattc attgaccttc tcctta                                  26

<210> SEQ ID NO 13
<211> LENGTH: 28
<212> TYPE: DNA
<213> ORGANISM: Bos taurus

<400> SEQUENCE: 13
actgaaagaa ttcaaagtac cccagctg                                28

<210> SEQ ID NO 14
<211> LENGTH: 27
<212> TYPE: DNA
<213> ORGANISM: Bos taurus

<400> SEQUENCE: 14
ggcctcgagt ccctctttca tactgtg                                 27

<210> SEQ ID NO 15
<211> LENGTH: 300
<212> TYPE: DNA
<213> ORGANISM: Bos taurus

<400> SEQUENCE: 15
ctaatatata tattgtagtc tcattccttc cttctctagt aaacagccag tttcacattc    60
```

```
gctgaggtgt aatatcttca actattgagc tgaatattga tctgytctca caaaccttt       120 tagagaagag ggcatttgga cttacatatt tatgattaat aaaaatttta ttatgcaaga      180
gcagtagtta aacagaatat gtatatgtgg tctattttac tgtattattg attctttcta     240
tctcttctcc ttgcactcaa acatatgatt tacaacttga tctcaattta cacactgagt     300

<210> SEQ ID NO 16
<211> LENGTH: 300
<212> TYPE: DNA
<213> ORGANISM: Bos taurus

<400> SEQUENCE: 16
ctaatatata tattgtagtc tcattccttc cttctctagt aaacagccag tttcacattc      60
gctgaggtgt aatatcttca actattgagc tgaatattga tctgctctca caaaccttt      120 tagagaagag ggsatttgga cttacatatt tatgattaat aaaaatttta ttatgcaaga     180
gcagtagtta aacagaatat gtatatgtgg tctattttac tgtattattg attctttcta    240
tctcttctcc ttgcactcaa acatatgatt tacaacttga tctcaattta cacactgagt    300

<210> SEQ ID NO 17
<211> LENGTH: 300
<212> TYPE: DNA
<213> ORGANISM: Bos taurus

<400> SEQUENCE: 17
actgacagct taaataaaga aaacttagca aggagataat acaagaaata atattgcaaa      60
aaatattagt gcattcacaa aaagcatatt tatttttaa tttgcagcag caaaatgtaa     120
gatacatttc tttttttttt ttttgatgg aatgaaaaaa aatttattta tattcatttt    180
ctccatttta tgttttaagg ttaacatttt atctytacta tcttgcatta tcaaatgaca    240
actcagaaat gcaagcttaa aagaggaatt ggtaaagtgg agaaagctgt gcagttctgt   300

<210> SEQ ID NO 18
<211> LENGTH: 410
<212> TYPE: DNA
<213> ORGANISM: Bos taurus

<400> SEQUENCE: 18
aaaattgagg taagtggcta tataatga acttatttca aaatttaaa ttataaaatt       60 taatatattt atcatcttat tttaaaacat tgtcattatg aaatgcttat aaagtgaatg    120
tcatgtgcat tatcctgtaa gaggaaacaa gaatatctgg gattctttag taggaatgat    180
aaattaataa caaaagcagg caatgctaat cttaagacag agataattc ccatgcatac    240 acattctcta aatttgcaca ggcaaagatc accagcaaat ttaacaattt tgagtcaaat   300
aaaatcttgc tgtttaaaaa taattgattt caaatttgta gatctayaga gtaaaatact   360
attatatgtc aaaaagtcat tagaataact ttatttcact tttcagttct                410

<210> SEQ ID NO 19
<211> LENGTH: 535
<212> TYPE: DNA
<213> ORGANISM: Bos taurus

<400> SEQUENCE: 19
gcttcttgtc cccaccacag tgttcttttc acctgccaat tcttcccctt atgagggagg      60
caggctccag gttttggctc acctgaaatc tgattttaaa aagatttctg ttgttttttg    120
```

```
catttctgat atgattctcc ataagattta agaagaattg taaaaaaaat atatggcatt      180
ttagtataaa catcattatt tttcatcact gtatctttat gtctggaatr gtacctgaca      240
tagcaagtag tcattgaata agtggataaa ttaataaata atttagctat ttatacatag      300
ggtcaattat gccactaatt tggtatgccc aaatgagcct ccacaattta gaaattaaga      360
ttttacattt ccttctccag gttttacatt ttgttgtgtt aatttcttct tgtaaagaac      420
tcatcgtatt caaatccatg tgtttctcaa tgaatctact tttatcagtc ttcattgccc      480
ttttctaatt atctgaagat aatttaatac ataattaatg aggaaatgtg tgatt          535

<210> SEQ ID NO 20
<211> LENGTH: 383
<212> TYPE: DNA
<213> ORGANISM: Bos taurus

<400> SEQUENCE: 20
tagtcattga ataagtggat aaattaataa ataatttagc tatttataca tagggtcaat       60
tatgccacta atttggtatg cccaaatgag cctccacaat ttagaaatta agattttaca      120
tttccttctc caggttttac attttgttgt gttaatttct tcttgtaaag aactcatcgt      180
attcaaatcc atgtgtttct caatgaatct acttttatca gtcttcattg ccttttcta       240 attatctgaa gataatttaa tacataatta atgaggaaat gtgtgattat aaggagagta      300
aaactgttat taattagctt cttgtctatc tcacaggaca agyaaacat gaagttcttc       360 atctttacct ccttttgctg ttg                                             383

<210> SEQ ID NO 21
<211> LENGTH: 367
<212> TYPE: DNA
<213> ORGANISM: Bos taurus

<400> SEQUENCE: 21
caaacataag tcctaaagta agtcctttca gataattaga aataggctaa gcaaagcaat       60
ggcaaagaaa aaaaaaaaag gtataaaact gatagaaaaa tgacaaaaga acagagaaaa      120
ccaaaactgc aagtcagttt taaagaattt aataatttta gcratttctt aacgtatcag      180
cccattgtca ttttgcataa tgattttgtt ttattaaaat ctagatttca attaggttaa      240
agggttttag gtgcaggaag caataacatt ttatgtttaa taagttattt agaaaataag      300
aataattaaa tgttccttca aagttgctga agtgtaaata tttaccactt tataaataaa      360
tattaat                                                               367

<210> SEQ ID NO 22
<211> LENGTH: 528
<212> TYPE: DNA
<213> ORGANISM: Bos taurus

<400> SEQUENCE: 22
ctgcaagtca gttttaaaga atttaataat tttagcaatt tcttaacgta tcagcccatt       60
gtcattttgc ataatgattt tgttttatta aaatctagat ttcaattagg ttaaagggtt      120
ttaggtgcag gaagcaataa cattttatgt ttaataagtt atttagaaaa taagaataat      180
taaatgttcc ttcaaagttg ctgaagtgta aatatttacc actttataaa taatattaa       240 trctactttt atttgttggg ttaaagaaac tggctatcag ttttcactca aacagtaaat      300
tatttcacaa acagttatta aaatcctacc atgtgctaag ttatcatact gaacactaga      360
aaatattaat aatagttaca ataatagca ttttggatac atgtatatgc atggctgaat       420
```

```
cccttttgctg ttcacttgaa actaccacaa cattgttaat caaatatatc ccaatacaaa    480
ataaatttta agtttgaaa aaaataataa cattctgcta aactagta                    528

<210> SEQ ID NO 23
<211> LENGTH: 744
<212> TYPE: DNA
<213> ORGANISM: Bos taurus

<400> SEQUENCE: 23
ctgcaagtca gttttaaaga atttaataat tttagcaatt tcttaacgta tcagcccatt     60
gtcattttgc ataatgattt tgttttatta aaatctagat ttcaattagg ttaaagggtt    120
ttaggtgcag gaagcaataa cattttatgt ttaataagtt atttagaaaa taagaataat    180
taaatgttcc ttcaaagttg ctgaagtgta aatatttacc actttataaa taaatattaa    240
tactactttt atttgttggg ttaaagaaac tggctatcag ttttcactca aacaktaaat    300
tatttcacaa acagttatta aaatcctacc atgtgctaag ttatcatact gaacactaga    360
aaatattaat aatagttaca aataatagca ttttggatac atgtatatgc atggctgaat    420
ccctttgctg ttcacttgaa actaccacaa cattgttaat caaatatatc ccaatacaaa    480
ataaatttta agtttgaaa aaaataataa cattctgcta aactagtatg gatgagtatg    540
tgtgggttct gtatatagac atacattatt tcttgaatat agatcgatag gtaatgtagt    600
attctgtttt cctttccagg ttggactgga aaatctatct tctacagttt catatctacc    660
actttacttc atacaaccag catgtttgga gtggtgcatc aataagacaa atcgcagagt    720 attcctgaa ttatttatac tctc                                             744

<210> SEQ ID NO 24
<211> LENGTH: 250
<212> TYPE: DNA
<213> ORGANISM: Bos taurus

<400> SEQUENCE: 24
ggttggactg gaaaatctat cttctacagt ttcatatcta ccactttact tcatacaacc     60
agcatgtttg gagtggtgca tcaataagac aaatcgcaga gtatttcctg aattatttat    120
actctcyctg ttagtttata ttgaaatatac tgggtttata tggtggtttc atacaaactt    180
agctgatgat tatttaaaat cctttcccta ctctttctga gttatagaaa tatttttctt    240
tccctctgag                                                            250

<210> SEQ ID NO 25
<211> LENGTH: 349
<212> TYPE: DNA
<213> ORGANISM: Bos taurus

<400> SEQUENCE: 25
gattgcaagt attggtactt tcctatgata tactgttagc ttaaaaatat atttgcaaat     60
gttgatacta tctatctcag agctataggt gaaaaattaa atactttat aaagaccaaa    120 ttgatcattt ttaaacgaaa ttcttatata ctgaaaatgt agatacataa cttcagtata    180
gatttatggt aaaataattk gaatcatttt tgtcaaattc tgtaaaaagt tgtcatacag    240
aataatttat aatattttg ttttcataga ataacatttt ctggtagaat atttcaaggc    300 cattttatt ttgtgtaatt aggttaataa aattaatttt ataaaggaa                349

<210> SEQ ID NO 26
```

<211> LENGTH: 375
<212> TYPE: DNA
<213> ORGANISM: Bos taurus

<400> SEQUENCE: 26

```
tttgtaaact gaagcagcct atataaaata atctgtcatt agtttgctga ctaaggtata      60
aacaaatttc atgtataatc taattttttct tatgtatctg aaacgcattt ttccagcaca    120
tataaatgta tgtattttttg ggtcttgcaa tttaatggaa ctctaggagt caaacgtgat    180
atgtttgact tatgattctg tttaatcatc ttcattcagt catgtcatgg atatatcaac    240
ccagcaaaat taagtaatag ctagatccckt ttaaaaattt aatgaaggtt aatagtttct    300
acataatgca caatgttttt catgaagact ctgaaagagc aggctaaagg ataaagacat    360
tttaaaaaat tacag                                                     375
```

<210> SEQ ID NO 27
<211> LENGTH: 716
<212> TYPE: DNA
<213> ORGANISM: Bos taurus

<400> SEQUENCE: 27

```
tttgtaaact gaagcagcct atataaaata atctgtcatt agtttgctga ctaaggtata      60
aacaaatttc atgtataatc taattttttct tatgtatctg aaacgcattt ttccagcaca    120
tataaatgta tgtattttttg ggtcttgcaa tttaatggaa ctctaggagt caaacgtgat    180
atgtttgact tatgattctg tttaatcatc ttcattcagt catgtcatgg atatatcaac    240
ccagcaaaat taagtaatag ctagatcctt ttaaaaattt aatgaaggtt aatagtttct    300
acataatgca caatgttttt catgaagact ctgaaagagc aggctaaagg ataaagacat    360
tttaaaaaat tacagatayt aaatgtaatt taccagtggg ttttagttta tcaattttaa    420
caaatccaat gatctaagag gaaatttctt tttaattttt tttgtagtat tttaaaattt    480
gtaatattta aatattgatg cttctctatt cctctgacaa aaccctacta ttactttcag    540
gatcaaatgc tttactttaa agtgtagtaa gatattggta tttcttatct tatataagca    600
ctaagcaaaa taatttgaat ggtaaatatt tatattgaag agcaaaatta aaaactaaat    660
gaataaaaat attactttca agtgcaacaa ctttttatcat aatatactcc tttgtt       716
```

<210> SEQ ID NO 28
<211> LENGTH: 461
<212> TYPE: DNA
<213> ORGANISM: Bos taurus

<400> SEQUENCE: 28

```
gtaatttacc agtgggtttt agtttatcaa ttttaacaaa tccaatgatc taagaggaaa     60
tttcttttta attttttttg tagtatttta aatttgtaa tatttaaata ttgatgcttc    120
tctattcctc tgacaaaacc ctactattac tttcaggatc aaatgcttta ctttaaagtg    180
tagtaagata ttggtatttc ttatcttata taagcactaa gcaaataat tgaatggta    240
aatatttata ttgaagagca aaattaaaaa ctaaatgaat aaaaatatta ctttcaagtg    300
caacaacttt tatcataata tactcctttg ttggaaaaat yaagaatttt ttttcatga    360
atcaaatttt attataagac ctaactattt tattttctta catagatctt gacaaccatg    420
agaattcctg cagcccgggg atccactagt tctagagcgc g                        461
```

<210> SEQ ID NO 29
<211> LENGTH: 155

<212> TYPE: DNA
<213> ORGANISM: Bos taurus

<400> SEQUENCE: 29

```
taccatggca cgtcacccac acccacattt atcatttatg gccattccac caaagaaaaa    60
tcaggataaa acagaaatcc ctaccatcaa taccattgct agtggcgagc ctacaagtac   120
acctaccayc gaagcagtag agagcactgt agcta                              155
```

<210> SEQ ID NO 30
<211> LENGTH: 205
<212> TYPE: DNA
<213> ORGANISM: Bos taurus

<400> SEQUENCE: 30

```
aagcagtaga gagcactgta gctactctag aagmttctcc agaagttatt gagagcccac    60
ctgagatcaa cacagtccaa gttcttcaa ctgcagtcta aaaactctaa ggagacatca   120
aagaagacaa cgcaggtcta gctgaaacca atgactact tcaaactttc ctttggccag   180
ttgtctgcct tcggtgaaca gagaa                                        205
```

<210> SEQ ID NO 31
<211> LENGTH: 1072
<212> TYPE: DNA
<213> ORGANISM: Bos taurus

<400> SEQUENCE: 31

```
ctcgagcaca gatttcagtt ctaggattca aacactccac tattaatgtc aagctacaaa    60
caaagtccaa ctaggggatt tttttagaac acttttttgg ctttaggtta tgttgtcaca   120
aacttgattt gctttgtcat atcatttttt ccctccatat gatgaaaagg atcagactac   180
ttcgcaaaat aattttctgt gaaaaaaaag aataaccatt atgagtatga gctgaatatt   240
cagttgtgtt taataaatag cctttttcac tttgctatca ttatttatat acttattctg   300
catttaaaaa caatgatcat gtgttccata atgtgagaga catgaaggag acaaaaataa   360
ggtaccaaac ttatcctcat taagctctat tctagacaaa gtcacagaaa tgcaatacaa   420
ggtaccagat gctaagttag agacatcaga aatatgtggt agtacaaaaa gatccagtga   480
tgcaccaaac ataagtccta aagtaagtcc tttcagataa ttagaaatag ctaagcaaa   540
gcaatggcaa agaaaaaaaa aaaaggtata aaactgatag aaaaatgaca aaagaaacag   600
agaaaccaaa actgcaagtc agttttaaag aatttaataa ttttagcaat tcttaacgt   660
atcagcccat tgtcattttg cataatgatt ttgtttatt aaaatctaga tttcaattag   720
gttaaagggt tttaggtgca ggaagcaata acatttatg tttaataagt tatttagaaa   780
ataagaataa ttaaatgttc cttcaaagtt gctgaagtgt aaatatttac cactttataa   840
ataaatatta atgctacttt tatttgttgg gttaaagaaa ctggctatca gttttcactc   900
aaacagtaaa ttatttcaca aacagttatt aaaatcctac catgtgctaa gttatcatac   960
tgaacactag aaaatattaa taatagttac aaataatagc attttggata catgtatatg  1020
catggctgga tccctttgct gttcacttga aactaccaca acattgttaa tc           1072
```

<210> SEQ ID NO 32
<211> LENGTH: 1115
<212> TYPE: DNA
<213> ORGANISM: Bos taurus

<400> SEQUENCE: 32

```
ctcgagcaca gattccagtt ctaggattca aacactccac tattaatgtc aagctacaaa    60
caaagtccaa ctaggggatt tttttagaac acttttttgg ctttaggtta tgttgtcaca   120
aacttgattt gctttgtcat atcatttttt ccctccatat gatgaaaagg atcagactac   180
ttcgcaaaat aattttctgt gaaaaaaaga gaataaccat tatgagtatg agctgaatat   240
tcagttgtgt ttaataaata gccttttttca ctttgctatc attatttata tacttattct   300
gcatttaaaa acaatgatca tgtgttccat aatgtgagag acatgaagga gacaaaaata   360
aggtaccaaa cttatcctca ttaagctcta ttctagacaa agtcacagaa atgcaataca   420
aggtaccaga tgctaagtta gagacatcag aaatatgtgg tagtacaaaa agatccagtg   480
atgcaccaaa cataagtcct aaagtaagtc ctttcagata attagaaata ggctaagcaa   540
agcaatggca aagaaaaaaa aaaaggtata aaactgatga aaaatgaca agagaaacag   600 agaaaccaaa actgcaagtc agttttaaag aatttaataa ttttagcgat tccttaacgt   660
atcagcccat tgtcattttg cataatgatt ttgttttatt aaaatctaga tttcaattag   720
gttaaagggt tttaggtgca ggaagcaata acattttatg tttaataagt tatttagaaa   780
ataagaataa ttaaatgttc cttcaaagtt gctgaagtgt aaatatttac cactttataa   840
ataaatatta atactacttt tatttgttgg gttaaagaaa ttggctatca gttttcactc   900
aaacattaaa ttatttcaca aacagttatt aaaatcctac catgtgctaa gttatcatac   960
tgaacactag aaatattaat aatagttaca ataatagca ttttggatac atgtatatgc   1020
atggctgaat ccctttgctg ttcacttgaa actaccacaa cattgttaat ccaatatatc   1080
cccataccaa atatatttta aagtttggaa aaaat                              1115

<210> SEQ ID NO 33
<211> LENGTH: 1103
<212> TYPE: DNA
<213> ORGANISM: Bos taurus

<400> SEQUENCE: 33 gcccctcga gcacagattt ccagttctag gattcaaaca ctccactatt aatgtcaagc    60
tacaaacaaa gtccaactag gggatttttt tagaacactt ttttggctta ggttatgttg   120
tcacaaactt gatttgcttt gtcatatcat tttttccctc catatgatga aaaggatcag   180
actacttcgc gaaataattt tctgtgaaaa aaagaataa ccattatgag tatgagctga   240
atattcagtt gtgttttaata aaaagccttt tcacttttgc tatcattatt tatatactta   300
ttctgcattt aaaaacaatg atcatgtgtt ccataatgtg agagacatga aggagacaaa   360
aataaggtac caaacttatc ctcattaagc tctattctag acaaagtcac agaaatgcag   420
tacaaggtac cagatgctaa gttagagaca tcagaaatat gtggtagtac aaaaagatcc   480
agtgatgcac caaacataag tcctaaagta agtcctttca gataattaga aataggctaa   540
gcaaagcaat ggcaaagaaa aaaaaaaggt ataaaactga tagaaaaatg acaaaagaaa   600
cagagaaacc aaaactgcaa gtcagtttta agaatttaa taattttagc aatttcttaa   660
cgtatcagcc cattgtcatt ttgcataatg attttgtttt attaagatct agatttcaat   720
taggttaaag ggttttaggt gcaggaagca ataacatttt atgtttaata agttatttag   780
aaaataagaa taattaaatg ttccttcaaa gttgctgaag tgtaaatatt taccacttta   840
taaataaata ttaatactac ttttatttgt tgggttaaag aaactggcta tcagttttca   900
ctcaaacagt aaattatttc acaaacagtt attaaaatcc taccatgtgc taagttatca   960
tactgaacac tagaaaatat taataatagt tacaaataat agcattttgg atacatgtat  1020
```

| | |
|---|---:|
| atgcatggct ggatcccttt gctgttcact tgaaactacc acaacattgt taatcaaata | 1080 |
| tatcccaata caaataagtt tta | 1103 |

<210> SEQ ID NO 34
<211> LENGTH: 907
<212> TYPE: DNA
<213> ORGANISM: Bos taurus

<400> SEQUENCE: 34

| | |
|---|---:|
| cgggccccct cgagcacaga tttccagttc taggattcaa acactccact attaatgtca | 60 |
| agctacaaac aaagtccaac taggggattt ttttagaaca cttttttggc tttaggttat | 120 |
| gttgtcacaa acttgatttg ctttgtcata tcattttttt ccctccatat gatgaaaagg | 180 |
| atcagactac ttcgcaaaat aatttttctgt gaaaaaaag aataaccatt atgagtatga | 240 |
| gctgaatatt cagttgtgtt taataaatag ccttttttcac tttgctatca ttatttatat | 300 |
| acttattctg catttaaaaa caatgatcat gtgttccata atgtgagaga catgaagaag | 360 |
| acaaaaataa ggtaccaaac ttatcctcat taagctctat tcaagacaaa gtcacagaaa | 420 |
| tgcaatacaa ggtaccagat gctaagttag agacatcaga aatatgtggt agtacaaaaa | 480 |
| gatccagtga tgcaccaaac ataagtccta agtaagtcc tttcagataa ttagaaatag | 540 |
| gctaagcaaa gcaatggcaa agaaaaaaaa aaaggtata aaactgatag aaaaatgaca | 600 |
| aaagaaacag agaaaccaaa actgcaagtc agttttaaag aatttaataa ttttagcaat | 660 |
| ttcttaacgt atcagcccat tgtcattttg cataatgatt ttgttttatt aaaatctaga | 720 |
| tttcaattag gttaaagggt tttaggtgca ggaagcaata acattttatg tttaataagt | 780 |
| tatttagaaa ataagaataa ttaatgttcc ttcaaagttg ctgaagtgta atatttacca | 840 |
| ctttattaaa taattattat tctacttttt tttgttgggt ttaaggaact ggctttcagt | 900 |
| tttcact | 907 |

<210> SEQ ID NO 35
<211> LENGTH: 1235
<212> TYPE: DNA
<213> ORGANISM: Bos taurus

<400> SEQUENCE: 35

| | |
|---|---:|
| cgggccccct cgagcacaga tttccagttc taggattcaa acactccact attaatgtcg | 60 |
| agctacaaac aaagtccaac taggggattt ttttagaaca cttttttggc tttaggttat | 120 |
| gttgtcacaa acttgatttg ctttgtcata tcattttttc cctccatatg atgaaaagga | 180 |
| tcagactact tcgcaaaata attttctgtg aaaaaaaga ataaccatta tgagtatgag | 240 |
| ctgaatattc agttgtgttt aataaatagc cttttttcact ttgctatcat tatttatata | 300 |
| cttattctgc atttaaaaca atgatcatgt gttccataat gtgagagaca tgaaggagac | 360 |
| aaaaataagg taccaaactt atcctcatta agctctattc tagacaaagt cacagaaatg | 420 |
| caatacaagg taccagatgc taagttagag acatcagaaa tatgtggtag tacaaaagaa | 480 |
| tccagtgatg caccaaacat aagtcctaaa gtaagtcctt tcagataatt agaaataggc | 540 |
| taagcaaagc aatggcaaag aaaaaaaaaa ggtataaaac tgatagaaaa atgacaaaag | 600 |
| aaacagagaa accaaaactg caagtcagtt ttaagaatt taataatttt agcgatttct | 660 |
| taacgtatca gcccattgtc attttgcata atgattttgt tttattaaaa tctagatttc | 720 |
| aattaggtta aagggttttta ggtgcaggga gcaataacat tttatgttta ataagttatt | 780 |

| | |
|---|---:|
| tagaaataag aataattaaa tgttccttca aagttgctga agtgtaaata tttaccactt | 840 |
| tataaataaa tatttatact acttttattt gttgggttaa agaaactggc tatcagtttt | 900 |
| cactcaaaca tttaattttt tcacaaacag ttttttaaat cctaccatgt gctaagtttt | 960 |
| catactgaac actagaaaat attaataata gttacaaata atagcatttt ggatacatgt | 1020 |
| atatgcatgg ctgaatccct tgctgatcc cttgaaacta ccacaacatt gttaatcaaa | 1080 |
| tatatcccat acaaaataaa ttttaaagat tgaaaaaaat aatacattct gctaacctag | 1140 |
| tatggatggg tatgtgtggg tccgtatatg gcatccataa ttcttgattt ggtcgatggg | 1200 |
| tatgtagtat ccgatttcct ttccggtagg caggg | 1235 |

<210> SEQ ID NO 36
<211> LENGTH: 1117
<212> TYPE: DNA
<213> ORGANISM: Bos taurus

<400> SEQUENCE: 36

| | |
|---|---:|
| gtacgggccc cctcgagcac agatttccag ttctaggatt aaacactcca ctattaatgt | 60 |
| caagctacaa acaaagtcca actagggat ttttttagaa cacttttttg gctttaggtt | 120 |
| atgttgtcac aaacttgatt tgctttgtca tatcatttt tccctccata tgatgaaaag | 180 |
| gatcagacta cttcgcaaaa taattttctg tgaaaaaaaa gaataaccat tatgagtatg | 240 |
| agctgaatat tcagttgtgt ttaataaata gccttttca ctttgctatc attatttata | 300 |
| tacttattct gcatttaaaa acaatgatca tgtgttccat aatgtgagag acatgaagga | 360 |
| gacaaaaata aggtaccaaa cttatcctca ttaagctcta ttctagacaa agtcacagaa | 420 |
| atgcaataca aggtaccaga tgctaagtta gagacatcag aaatatgtgg tagtacaaaa | 480 |
| agatccagtg atgcaccaaa cataagtcct aaagtaagtc ctttcagata attagaaatg | 540 |
| ggctaagcaa agcaatggca aagaaaaaaa aaaaggtat aaaactgata gaaaatgac | 600 |
| aaaagaaaca gagaaaccaa aactgcaagt cagttttaaa gaatttaata attttagcaa | 660 |
| tttcttaacg tatcagccca ttgtcatttt gcataatgat tttgttttat taaaatctag | 720 |
| atttcaatta ggttaaaggg ttttaggtgc aggaagcaat aacattttat gtttaataag | 780 |
| ttatttagaa aataagaata attaaatgtt ccttcaaagt tgctgaagtg taaatattta | 840 |
| ccactttata aataaatatt aatactactt ttatttgttg ggttaaagaa actggctatc | 900 |
| agttttcact caaacagtaa attatttcac aaacagttat taaatcccca ccatgtgcta | 960 |
| agttatcata ctgaacacta gaaaatatta ataatagtta caaataatag catttggata | 1020 |
| catgtatatg catggctgaa tccctttgct gttcacttga aactacccca acattgttat | 1080 |
| caaatatatc ccaataccaa ataaatttaa aagattg | 1117 |

<210> SEQ ID NO 37
<211> LENGTH: 1121
<212> TYPE: DNA
<213> ORGANISM: Bos taurus

<400> SEQUENCE: 37

| | |
|---|---:|
| gtacgggccc cctcgagcac agatttccag ttctaggatt caaacactcc actattaatg | 60 |
| tcaagctaca aacaaagtcc aactagggga tttttttaga acacttttt ggctttaggt | 120 |
| tatgttgtca caaacttgat tgctttgtc atatcatttt tccctccat atgatgaaaa | 180 |
| ggatcagact acttcgcaaa ataattttct gtgaaaaaaa agaataacca ttatgagtat | 240 |
| gagctgaata ttcagttgtg tttaataaat agccttttc actttgctat cattatttat | 300 |

```
atacttattc tgcatttaaa aacaatgatc atgtgttcca taatgtgagg gacatgaagg      360
agacaaaaat aaggtaccaa acttatcctc attaagctct attctagaca aagtcacaga      420
aatgcaatac aaggtaccag atgctaagtt agagacatca gaaatatgtg gtagtacaaa      480
aagatccagt gatgcaccaa acataagtcc taaagtaagt cctttcagat aattagaaat      540
aggctaagca aagcaatggc aaagaaaaaa aaaaaggta taaaactgat agaaaaatga      600
caaaagaaac agagaaacca aaactgcaag tcagttttaa agaatttaat aattttagca      660
atttcttaac gtatcagccc attgtcattt tgcataatga ttttgtttta ttaaaatcta      720
gatttcaatt aggttaaagg gttttaggtg caggaagcaa taacatttta tgtttaataa      780
gttatttaga aaataagaat aattaaatgt tccttcaaag ttgctgaagt gtaaatattt      840
accactttat taataaatat taatactact tttatttgtt gggttaaaga aactggctat      900
cagttttcac tcaaacagta aattatttca caaacagtta ttaaaatcct accatgtgct      960
aagttatcat actgaaccct agaaaatatt aataatagtt accaataata gccttttagg     1020
atacctgtat atgcctggct gaatcccttt gctgttccct tgaaactacc ccaacattgt     1080
aaatcaatat atccccatac aaaataaatt ttaaagtttg g                         1121

<210> SEQ ID NO 38
<211> LENGTH: 1125
<212> TYPE: DNA
<213> ORGANISM: Bos taurus

<400> SEQUENCE: 38
gtacgggccc cctcgagcac agatttccag ttctaggatt caaacactcc actattaatg       60
tcaagctaca aacaaagtcc aactagggga ttttttttaga acactttttt ggctttaggt     120
tatgttgtca caaacttgat ttgctttgtc atatcatttt ttccctccat atgatgaaaa      180
ggatcagact acttcgcaaa ataatttttct gtgaaaaaaa agaataacca ttatgagtat      240
gagctgaata ttcagttgtg tttaataaat agccttttc actttgctat cattatttat       300
atacttattc tgcatttaaaa aacaatgatc atgtgttcca taatgtgaga gacatgaagg      360
agacaaaaat aaggtaccaa acttatcctc attaagctct attctagaca aagtcacaga      420
aatgcaatac aaggtaccag atgctaagtt agagacatca gaaatatgtg gtagtacaaa      480
aagatccagt gatgcaccaa acataagtcc taaagtaagt cctttcagat aattagaaat      540
aggctaagca aagcaatggc aaagaaaaaa aaaaaggtat aaaactgata gaaaaatgac      600
aaaagaaaca gagaaaccaa aactgcaagt cagttttaaa gaatttaata attttagcga      660
tttcttaacg tatcagccca ttgtcatttt gcataatgat tttgttttat taaaatctag      720
atttcaatta ggttaaaggg ttttaggtgc aggaagcaat aacattttat gtttaataag      780
ttatttagaa aataagaata attaaatgtt ccttcaaagt tgctgaagtg taaatattta      840
ccactttata ataaatatt aatgctactt ttatttgttg ggttaaagaa actggctatc       900
agctttcact cacacattaa attatttcac aaacagttat aaatcctac catgtgctaa      960 gttatcatac tgaacactag aaatattaat aatagttaca ataatagcat tttgggtaca     1020
tgtatatgca tggctggatc cctttgctgt tcacttgaaa ctaccacaac attgttaatc     1080
aatatatccc aatacaaaat aaattttaag tttgaaaaaa ataat                     1125

<210> SEQ ID NO 39
<211> LENGTH: 1143
<212> TYPE: DNA
```

<213> ORGANISM: Bos taurus

<400> SEQUENCE: 39

```
gtacgggccc cctcgagcac agatttccag ttctaggatt caaacactcc actattaatg    60
tcaagctaca aacaaagtcc aactagggga ttttttttaga acactttttt ggctttaggt   120
tatgttgtca caaacttgat ttgctttgtc atatcatttt ttccctccat atgatgaaaa   180
ggatcagact acttcgcaga ataattttct gtgaaaaaaa agaataacca ttatgagtat   240
gagctgaata ttcagttgtg tttaataaat agcctttttc actttgctat cattatttat   300
atacttattc tgcatttaaa acaatgatc atgtgttcca taatgtgaga gacatgaagg   360
agacaaaaat aaggtaccaa acttatcctc attaagctct attctagaca aagtcacaga   420
aatgcaatac aaggtaccag atgctaagtt agagacatca gaaatatgtg gtagtacaaa   480
aagatccagt gatgcaccaa acataagtcc taaagtaagt cctttcagat aattagaaat   540
aggctaagca aagcaatggc aaagaaaaaa aaaaaggta taaaactgat agaaaaatga   600
caaaagaaac agagaaacca aaactgcaag tcagttttaa agaatttaat aattttagcg   660
atttcttaac gtatcagccc attgtcattt tgcataatga ttttgttta ttaaaatcta   720
gatttcaatt aggttaaagg gttttaggtg caggaagcaa taacatttta tgtttaataa   780
gttatttaga aaataagaat aattaaatgt tccttcaaag ttgctgaagt gtaaatattt   840
accactttat aaataaatat taatactact tttatttgtt gggttaaaga aactggctat   900
cagttttcac tcaaacatta aattatttca caaacagtta ttaaaatcct accatgtgct   960
aagttatcat actgaacact agaaaatatt aataatagtt acaaataata gcattttggg  1020
tacatgtata tgcatggctg aatcccttg ctgttcactt gaaactaccc caacattgtt  1080
aatccaatat atcccaatac acaataaatt ttaaagtttg aaaaaataat aacattctgc  1140
taa                                                                 1143
```

<210> SEQ ID NO 40
<211> LENGTH: 1214
<212> TYPE: DNA
<213> ORGANISM: Bos taurus

<400> SEQUENCE: 40

```
gtacgggccc cctcgagcac agatttccag ttctaggatc aaacactcca ctattaatgt    60
caagctacaa acaaagtcca actagggat ttttttagaa cacttttttg gctttaggtt    120
atgttgtcac aaacttgatt tgctttgtca tatcatttt tccctccata tgatgaaaag   180
gatcagacta cttcgcaaaa taattttctg tgaaaaaaaa gaataaccat tatgagtatg   240
agctgaatat tcagttgtgt ttaataaata gcctttttca ctttgctatc attatttata   300
tacttattct gcatttaaaa acaatgatca tgtgttccat aatgtgagag acatgaagga   360
gacaaaaata aggtaccaaa cttatcctca ttaagctcta ttctagacaa agtcacagaa   420
atgcaataca aggtaccaga tgctaagtta gagacatcag aaatatgtgg tagtacaaaa   480
agatccagtg atgcaccaaa cataagtcct aaagtaagtc ctttcagata attagaaata   540
ggctaagcaa agcaatggca agaaaaaaa aaggtataa aactgataga aaatgacaa   600
aagaaacaga gaaaccaaaa ctgcaagtca gttttaaaga atttaataat tttagcgatt   660
tcttaacgta tcagcccatt gtcattttgc ataatgattt tgttttatta aaatctagat   720
ttcaattagg ttaaagggtt ttaggtgcag gaagcaataa catttatgt ttaataagtt   780
atttagaaaa taagaataat taaatgttcc ttcaaagttg ctgaagtgta aatatttacc   840
```

```
actttataaa taaatattaa tactactttt atttgttggg ttaaagaaac tggctatcag    900
ttttcactca acattaaat tatttcacaa acagttatta aaatcctacc atgtgctaag    960
ttatcatact gaacactaga aaatattaat aatagttaca ataatagca ttttggatac   1020 atgtatatgc atggctgaat ccctttgctg ttcacttgaa actaccacaa cattgttatc   1080
aaatatatcc caatacaaaa tatattttaa agtttggaaa aataaataca ttctgctaaa   1140
ctagtatggg tgggtatgtg tgggttctgt atataggcat acattatttc ttgaatatag   1200
gtcggtgggt aatg                                                    1214
```

<210> SEQ ID NO 41
<211> LENGTH: 914
<212> TYPE: DNA
<213> ORGANISM: Bos taurus

<400> SEQUENCE: 41

```
agtttaaaag aatttaaaaa atttagcaat ttcttatcgt atcagcccta ttgccatttt     60
gcaaaatgat tttgtttaat aaaaatctag atttcaatta ggttaaaggg ttttaggtgc    120
aggaagcaat aacattttat gtttaataag ttatttagaa aataagaata attaaaatgt    180
tccttcaaag ttgctgaagt gtaaatattt accactttat aaataaatat taatactact    240
tttatttgtt gggttaaaga aactggctat cagttttcac tcaaacagta aattatttca    300
caaacagtta ttaaaatcct accatgtgct aagttatcat actgaacact agaaaatatt    360
aataatagtt acaaataata gcattttgga tacatgtata tgcatggctg aatccctttg    420
ctgttcactt gaaactacca caacattgtt aatcaaatat atcccaatac aaaataaatt    480 ttaaagttttg aaaaaataa taacattctg ctaaactagt atggatgagt atgtgtgggt    540
tctgtatata gacatacatt atttcttgaa tatagatcga taggtaatgt agtattctgt    600 tttcctttc aggttggact ggaaaatcta tcttctacag tttcatatct accactttac     660
ttcatacaac cagcatgttt ggagtggtgc atcaataaga caaatcgcag agtatttcct    720
gaattattta tactctccct gttagtttat attgaatata ctgggtttat atggtggttt    780
catacaaact tagctgatga ttatttaaaa tcctttccct actctttctg agttatagaa    840
atattttcct ttccctctga gaataaaatt tcaagtgaat tcctgcagcc cggggatcca    900
ctagttctag agcg                                                     914
```

<210> SEQ ID NO 42
<211> LENGTH: 1121
<212> TYPE: DNA
<213> ORGANISM: Bos taurus
<220> FEATURE:
<221> NAME/KEY: modified_base
<222> LOCATION: (1086)
<223> OTHER INFORMATION: a, c, g, t, unknown or other

<400> SEQUENCE: 42

```
atgcaataca aggtaccaga tgctaagtag agacatcaga aatatggggt agtacaaaaa     60
gatccagtgt tgcaccaaac ataagtccta agtaagtcc tttcagataa ttagaaatag    120
gctaagcaaa gcaatggcaa agaaaaaaaa aaaggtataa aactgataga aaatgacaa    180 gagaaacaga gaaaccaaaa ctgcaagtca gttttaaaga atttaataat tttagcgatt    240
tcttaacgta tcagcccatt gtcattttgc ataatgattt tgttttatta aaatctagat    300
ttcaattagg ttaaagggtt ttaggtgcag gaagcaataa cattttatgt ttaataagtt    360
```

```
atttagaaaa taagaataat taaatgttcc ttcaaagttg ctgaagtgta aatatttacc      420
actttataaa taaatattaa tactactttt atttgttggg ttaaagaaat tggctatcag      480
ttttcactca aacattaaat tatttcacaa acagttatta aaatcctacc atgtgctaag      540
ttatcatact gaacactaga aaatattaat aatagttaca ataatagca ttttggatac       600 atgtatatgc atggctgaat cccttttgctg ttcacttgaa actaccacaa cattgttaat    660
caaatatatc ccaatacaaa ataaatttta aagtttgaaa aaaataataa cattctgcta     720
aactagtatg gatgagtatg tgtgggttct gtatatagac atacattatt tcttgaatat    780
agatcgatag gtaatgtagt attctgtttt cctttttcagg ttggactgga aaatctatct   840
tctacagttt catatctacc actttacttc atacaaccag catgtttgga gtggtgcatc   900
aataagacaa atcgcagagt atttcctgaa ttatttatac tctctctgtt agtttatatt   960
gaatatactg ggtttatatg gtggcttcat acaaacttag ctgatgatta tttaaaatcc   1020
tttccctact ctttctgagt tatagaaata tttttcttttc cctctgagaa taaaatttca  1080
agtganktcc tgcagcccgg ggatccacta gttctagagc g                        1121
```

<210> SEQ ID NO 43
<211> LENGTH: 1129
<212> TYPE: DNA
<213> ORGANISM: Bos taurus

<400> SEQUENCE: 43

```
cacagtaatg caaaacaagg taccagatgc taagttagag acaccagaaa tatggggagt       60
acaaaaagac ccagggatgc accaaacaaa agtcctaaag taagtccttc tagaaaatta      120
gaaataggct aagcaaagca atggcaaaga aaaaaaaaaa aggtataaaa ctgatagaaa      180
aatgacaaaa gaaacagaga accaaaaact gcaagtcagt tttaaagaat taataatttt     240
tagcaatttc ttaacgtatc agcccattgt cattttgcat aatgattttg ttttattaaa     300
atctagattt caattaggtt aaagggtttt aggtgcagga agcaataaca ttttatgttt     360
aataagttat ttagaaaata agaataatta aatgttcctt caaagttgct gaagtgtaaa     420
tatttaccac tttataaata aatattaata ctacttttat ttgttgggtt aaagaaactg     480
gctatcagtt ttcactcaaa cagtaaatta tttcacaaac agttattaaa atcctaccat    540
gtgctaagtt atcatactga acactagaaa atattaataa tagttacaaa taatagcatt    600
ttggatacat gtatatgcat ggctgaatcc ctttgctgtt cacttgaaac taccacaaca    660
ttgttaatca aatatatccc aatacaaaat aaattttaaa gtttgaaaaa aataataaca    720
ttctgctaaa ctagtatgga tgagtatgtg tgggttctgt atatagacat acattatttc   780
ttgaatatag atcgataggt aatgtagtat tctgttttcc ttttcaggtt ggactggaaa    840
atctatcttc tacagtttca tatctaccac tttacttcat acaaccagca tgtttggagt    900
ggtgcatcaa taagacaaat cgcagagtat ttcctgaatt atttatactc tcctgttag     960 tttatattga atatactggg tttatatggt ggtttcatac aaacttagct gatgattatt   1020
taaaatcctt tccctactct ttctgagtta tagaaatatt tttctttccc tctgagaata  1080
aaatttcaag tgaattcctg cagcccgggg atccactagt tctagagcg               1129
```

<210> SEQ ID NO 44
<211> LENGTH: 1133
<212> TYPE: DNA
<213> ORGANISM: Bos taurus

<400> SEQUENCE: 44

```
aagtcacagt aatgcaatac aggtaccaga tgctaagtta gagacatcag aaatatgtgg      60
tagtacaaaa agatccagtg atgcaccaaa cataagtcct aaagtaagtc ctttcagata     120
attagaaatg ggctaagcaa agcaatggca aagaaaaaaa aaaaggtat  aaaactgata     180 gaaaatgac  aaaagaaaca gagaaaccaa aactgcaagt cagttttaaa gaatttaata     240 atttagcaa  tttcttaacg tatcagccca ttgtcatttt gcataatgat tttgttttat     300
taaaatctag atttcaatta ggttaaaggg ttttaggtgc aggaagcaat aacattttat     360
gtttaataag ttatttagaa ataagaata  attaaatgtt ccttcaaagt tgctgaagtg     420
taaatattta ccactttata aataaatatt aatactactt ttatttgttg ggttaaagaa     480
actggctatc agttttcact caaacagtaa attatttcac aaacagttat taaaatccca     540
ccatgtgcta agttatcata ctgaacacta gaaaatatta ataatagtta caaataatag     600
cattttggat acatgtatat gcatggctga atccctttgc tgttcacttg aaactaccac     660
aacattgtta atcaaatata tcccaataca aaataaattt taaagtttga aaaaaataat     720
aacattctgc taaactagta tggatgagta tgtgtgggtt ctgtatatag acatacatta     780
tttcttgaat atagatcgat aggtaatgta gtattctgtt ttcctttca ggttggactg      840 gaaaatctat cttctacagt ttcatatcta ccactttact tcatacaatc agcatgtttg     900
gagtggtgca tcaataagac aaatcgcaga gtatttcctg aattatttat actctccctg     960
ttagtttata ttgaatatac tgggtttata tggtggtttc atacaaactt agctgatgat    1020
tatttaaaat cctttcccta ctctttctga gttatagaaa ttttttctt tccctctgag     1080 aataaaattt caagtgaatt cctgcagccc ggggatccac tagttctaga gcg            1133

<210> SEQ ID NO 45
<211> LENGTH: 1146
<212> TYPE: DNA
<213> ORGANISM: Bos taurus
<220> FEATURE:
<221> NAME/KEY: modified_base
<222> LOCATION: (1115)
<223> OTHER INFORMATION: a, c, g, t, unknown or other

<400> SEQUENCE: 45
taagctctat ctagacaaag tcacagaatg caaacaagg  accagatgct aagttagaga      60
catcagaaat atgtggtagt acaaaagat  ccagtgatgc accaaacata agtcctaaag     120
taagcccttt cagataatta gaaataggct aagcaaagca atggcaaaga aaaaaaaaa     180 aggtataaaa ctgatagaaa atgacaaaa  gaaacagaga accaaaact  gcaagtcagt     240 tttaaagaat ttaataattt tagcgatttc ttaacgtatc agcccattgt catttttgcat    300 aatgattttg ttttattaaa atctagattt caattaggtt aaagggtttt aggtgcagga    360
agcaataaca ttttatgttt aataagttat ttagaaaata agaataatta atgttccttc    420
caaagttgct gaagtgtaaa tatttaccac tttataaata aatattaata ctacttttat    480
ttgtttgggt taagaaact  ggctatcagt tttcactcaa acattaaatt atttcacaaa    540
cagttattaa aatcctacca tgtgctaagt tatcatactg aacactagaa atattaata    600 atagttacaa ataatagcat tttggataca tgtatatgca tggctgaatc cctttgctgt    660
tcacttgaaa ctaccacaac attgttaatc aaatatatcc aatacaaaaa taaatttaa     720 agtttgaaaa aaataataac attctgctaa actagtatgg atgagtatgt gtgggttctg    780
tatatagaca tacattattt cttgaatata gatcgatagg taatgtagta ttctgttttc    840
```

```
cttttcaggt tggactggaa aatctatctt ctacagtttc atatctacca ctttacttca      900
tacaaccagc atgtttggag tggtgcatca ataagacaaa tcgcagagta tttcctgaat      960
tatttatact ctctctgtta gtttatattg aatatactgg gtttatatgg tggtttcata     1020
caaacttagc tgatgattat ttaaaatcct ttccctactc tttctgagtt atagaaatat     1080
ttttccttcc ctctgagaat aaaatttcaa gtganktcct gcagcccggg gatccactag     1140
ttctag                                                                1146
```

<210> SEQ ID NO 46
<211> LENGTH: 1141
<212> TYPE: DNA
<213> ORGANISM: Bos taurus

<400> SEQUENCE: 46

```
aactatcctc ataagcccat tccagacaag cacagaatgc aaacaagtac cagtgctaag       60
ttggtcatca gaatatgggt agtacaaaag atccagggag caccaaacat aagtccttaa      120
gtaagtcctt cagatattag aaataggcta agcaaagcaa tggcaaagaa aaaaaaaagg      180
tataaaactg atagaaaaat gacaaaagaa acagagaatc caaaacttca agtcagtttt      240
aaagaattta ataattttag cgatttctta acgtatcagc ccattgtcat tttgcataat      300
gattttgttt aattaaaacc tagattccaa ttaggttaaa gggttttagg tgcaggaagc      360
aataacattt tatgtttaaa aatttattta gaaataagaa aaattaaatg ttccttcaaa      420
gttgctgaag tgtaaatatt taccacttta taaataaata ttaatactac ttttatttgt      480
tgggttaaag aaactggcta tcagtttcac tcaaacatta aattatttca caaacagtta      540
ttaaaatcct accatgtgct aagttatcat actgaacact agaaaatatt aataatagtt      600
acaaataata gcattttgga tacatgtata tgcatggctg aatcccttttg ctgttcactt      660 gaaactacca caacattgtt aatcaaatat atcccaatac aaaataaatt ttaaagtttg      720
aaaaaaataa taacattctg ctaaactagt atggatgagt atgtgtgggt tctgtatata      780
gacatacatt atttcttgaa tatagatcga taggtaatgt agtattctgt tttccttttc      840
aggttggact ggaaaatcta tcttctacag tttcatatct accactttac ttcatacaac      900
cagcatgttt ggagtggtgc atcaataaga caaatcgcag agtatttcct gaattattta      960
tactctctct gttagtttat attgaatata ctgggtttat atggtggttt catacaaact     1020
tagctgatga ttatttaaaa tcctttccct actctttctg agttatagaa atattttttct     1080 ttccctctga gaataaaatt tcaagtgaat tcctgcagcc cggggatcca ctagttctag     1140
a                                                                    1141
```

<210> SEQ ID NO 47
<211> LENGTH: 1168
<212> TYPE: DNA
<213> ORGANISM: Bos taurus

<400> SEQUENCE: 47

```
accaaactta tccccattaa gccctatcct agacaaagtc acagaaatgc agtacaaggt       60
accagatgct tagttagaga catcagaaat atgtggtagt acaaaaaaga tccagtgatg      120
caccaaacat aagtcctaaa gtaagtcctt tcagataatt agaaataggc taagcaaagc      180
aatggcaaag aaaaaaaaaa ggtataaaaa ctgatagaaa aatgacaaaa gaaacagaga      240
aaccaaaact gcaagtcagt tttaaagaat ttaataattt tagcaatttc ttaacgtatc      300
agcccattgt cattttgcat aatgattttg tttttattaag atctagattt caattaggtt      360
```

```
aaagggtttt aggtgcagga agcaataaca ttttatgttt aataagttat ttagaaaata      420
agaataatta aatgttcctt caaagttgct gaagtgtaaa tatttaccac tttataaata      480
aatattaata ctacttttat ttgttgggtt aaagaaactg gctatcagtt ttcactcaaa      540
cagtaaatta tttcacaaac agttattaaa atcctaccat gtgctaagtt atcatactga      600
acactagaaa atattaataa tagttacaaa taatagcatt tggatacat gtatatgcat       660 ggctgaatcc ctttgctgtt cacttgaaac taccacaaca ttgttaatca aatatatccc      720
aatacaaaat aagttttaaa gtttgaaaaa aataataaca ttctgctaaa ctagtatgga      780
tgagtatgtg tgggttctgt atatagacat acattatttc ttgaatatag atcgataggt     840
aatgtagtat tctgttatcc ttttcaggtt ggactggaaa atctatcttc tacagtttca      900
tatctaccac tttacttcat acaaccagca tgtttggagt ggtgcatcaa taagacaaat     960
cgcagagtat ttcctgaatt atttatactc tccctgttag tttatattga atatactggg    1020
tttatatggt ggtttcatac aaacttagct gatgattatt taaaatcctt tccctactct    1080
ttctgagtta tagaaatatt tttctttccc tctgagaata aatttcaag tgaattcctg     1140 cagcccgggg atccactagt tctagagc                                        1168
```

<210> SEQ ID NO 48  
<211> LENGTH: 1177  
<212> TYPE: DNA  
<213> ORGANISM: Bos taurus

<400> SEQUENCE: 48

```
aaataaggta ccaaacttat cctcattaag ctctattcta gacaaagtca cagaaatgca      60
atacaaggta ccagatgcta agttagagac atcagaaata tgtggtagta caaaaagatc     120
cagtgatgca ccaaacataa gtcctaaagt aagtcctttc agataattag aaataggcta     180
agcaaagcaa tggcaaagaa aaaaaaaaaa ggtataaaac tgatagaaaa atgacaaaag     240
aaacagagaa accaaaactg caagtcagtt ttaagaatt taataatttt agcaatttct      300
taacgtatca gcccattgtc attttgcata atgattttgt tttattaaaa tctagatttc     360
aattaggtta aagggtttta ggtgcaggaa gcaataacat tttatgttta ataagttatt     420
tagaaaataa gaataattaa atgttccttc aaagttgctg aagtgtaaat atttaccact     480
ttataaataa atattaatgc tactttttatt tgttgggtta agaaactgg ctatcagtttt    540 tcactcaaac agtaaattat ttcacaaaca gttattaaaa tcctaccatg tgctaagtta     600
tcatactgaa cactagaaaa tattaataat agttacaaat aatagcattt ggatacatg      660 tatatgcatg gctgaatccc tttgctgttc acttgaaact accacaacat tgttaatcaa     720
atatatccca atacaaaata aattttaaag tttgaaaaaa ataataacat tctgctaaac     780
tagtatggat gagtatgtgt gggttctgta tatagacata cattatttct tgaatataga    840
tcgataggta atgtagtatt ctgttttcct tttcaggttg gactggaaaa tctatcttct     900
acagtttcat atctaccact ttacttcata caaccagcat gtttggagtg gtgcatcaat     960
aagacaaatc gcagagtatt tcctgaatta tttatactct ccctgttagt ttatattgaa    1020
tatactgggt ttatatggtg gtttcataca aacttagctg atgattattt aaaatccttt     1080
ccctactctt tctgagttat agaaatattt ttctttccct ctgagaataa aatttcaagt    1140
gaattcctgc agcccgggga tccactagtt ctagagc                              1177
```

<210> SEQ ID NO 49

<211> LENGTH: 1190
<212> TYPE: DNA
<213> ORGANISM: Bos taurus

<400> SEQUENCE: 49

```
agagacagta ggagacaaaa ataggtacca aacttatccc cattaagctc tattctagac      60
aaagtcacag aaatgcaata catggtacca gatgcttagt tagagacatc agaaatatgt     120
ggtagtacaa aaagatccag tgatgcacca acataagtc ctaaagtaag tcctttcaga      180
taattagaaa taggctaagc aaagcaatgg caaagaaaaa aaaaaaggta taaaactgat     240
agaaaatga caaagaaac agagaaacca aaactgcaag tcagttttaa agaatttaat       300
aattttagcg atttcttaac gtatcagccc attgtcattt tgcataatga ttttgtttta    360
ttaaaatcta gatttcaatt aggttaaagg gttttaggtg caggaagcaa taacatttta    420
tgtttaataa gttatttaga aaataagaat aattaaatgt tccttcaaag ttgctgaagt    480
gtaaatattt accactttat aaataaatat taatgctact tttatttgtt gggttaagaa    540
aactggctat cagctttcac tcaaacatta aattatttca caaacagtta ttaaaatcct    600
accatgtgct aagttatcat actgaacact agaaaatatt aataatagtt acaataata     660
gcattttgga tacatgtata tgcatggctg aatccctttg ctgttcactt gaaactacca    720
caacattgtt aatcaaatat atcccaatac aaaataaatt ttaaagtttg aaaaaaataa    780
taacattctg ctaaactagt atggatgagt atgtgtgggt tctgtatata gacatacatt    840
atttcttgaa tatagatcga taggtaatgt agtattctgt tttcctttc aggttggact     900
ggaaaatcta tcttctacag tttcatatct accactttac ttcatacaac cagcatgttt    960
ggagtggtgc atcaataaga caaatcgcag agtatttcct gaattattta tactctctct   1020
gttagtttat attgaatata ctgggtttat atggtggttt catacaaact agctgatga    1080
ttatttaaaa tccttccct actctttctg agttatagaa atatttttct ttccctctga    1140
gaataaaatt tcaagtgaat tcctgcagcc cggggatcca ctagttctag              1190
```

<210> SEQ ID NO 50
<211> LENGTH: 1205
<212> TYPE: DNA
<213> ORGANISM: Bos taurus

<400> SEQUENCE: 50

```
gtcccataat ggagagacat gagggacaa aaataggtac caaacttacc cccattaagc      60
cctatcctag acaaagtcac agaaatgcaa tacaaggtac cagatgctaa gttagagaca    120
tcagaaatat gtggtagtac aaaaagatcc agtgatgcac caaacataag tcctaaagta    180
agtcctttca gataattaga aataggctaa gcaaagcaat ggcaaagaaa aaaaaaaggt    240
ataaaactga tagaaaaatg acaaaagaaa cagagaaacc aaaactgcaa gtcagtttta    300
aagaatttaa taattttagc gatttcttaa cgtatcagcc cattgtcatt tgcataatg     360
attttgtttt attaaaatct agatttcaat taggttaaag ggttttaggt gcaggaagca    420
ataacatttt atgtttaata agttatttag aaaataagaa taattaaatg ttccttcaaa    480
gttgctgaag tgtaaatatt taccacttta taaataaata ttaatactac ttttatttgt    540
tgggttaaag aaactggcta tcagttttca ctcaaacatt aaattatttc acaaacagtt    600
attaaaatcc taccatgtgc taagttatca tactgaacac tagaaaatat taataatagt    660
tacaaataat agcattttgg atacatgtat atgcatggct gaatccctt gctgttcact     720
tgaaactacc acaacattgt taatcaaata tatcccaata caaaataaat tttaaagttt    780
```

```
gaaaaaaata ataacattct gctaaactag tatggatgag tatgtgtggg ttctgtatat    840
agacatacat tatttcttga atatagatcg ataggtaatg tagtattctg ttttcctttt    900
caggttggac tggaaaatct atcttctaca gtttcatatc taccacttta cttcatacaa    960
ccagcatgtt tggagtggtg catcaataag acaaatcgca gagtatttcc tgaattattt   1020
atactctctc tgttagttta tattgaatat actgggttta tatggtggtt tcatacaaac   1080
ttagctgatg attatttaaa atcctttccc tactcttcct gagttataga aatattttc    1140 tttccctctg agaataaaat ttcaagtgaa ttcctgcagc ccggggatcc actagttcta   1200
gagcg                                                              1205

<210> SEQ ID NO 51
<211> LENGTH: 1544
<212> TYPE: DNA
<213> ORGANISM: Bos taurus

<400> SEQUENCE: 51
gtacgggccc cctcgagcac agatttccag ttctaggatt caaacactcc actattaatg     60
tcaagctaca aacaaagtcc aactagggga ttttttaga acactttttt ggctttaggt    120
tatgttgtca caaacttgat ttgctttgtc atatcattt ttccctccat atgatgaaaa    180
ggatcagact acttcgcaaa ataattttct gtgaaaaaaa agaataacca ttatgagtat    240
gagctgaata ttcagttgtg tttaataaat agccttttc actttgctat cattatttat    300
atacttattc tgcatttaaa aacaatgatc atgtgttcca taatgtgaga gacatgaagg    360
agacaaaaat aaggtaccaa acttatcctc attaagctct attctagaca aagtcacaga    420
aatgcaatac aaggtaccag atgctaagtt agagacatca gaaatatgtg gtagtacaaa    480
aagatccagt gatgcaccaa acataagtcc taaagtaagt cctttcagat aattagaaat    540
aggctaagca aagcaatggc aaagaaaaaa aaaaaggta taaaactgat agaaaaatga    600
caaaagaaac agagaaacca aaactgcaag tcagttttaa agaatttaat aattttagcr    660
atttcttaac gtatcagccc attgtcattt tgcataatga ttttgtttta ttaaaatcta    720
gatttcaatt aggttaaagg gttttaggtg caggaagcaa taacatttta tgtttaataa    780
gttatttaga aaataagaat aattaaatgt tccttcaaag ttgctgaagt gtaaatattt    840
accactttat aaataaatat taatactact tttatttgtt gggttaaaga aactggctat    900
cagttttcac tcaaacatta aattatttca caaacagtta ttaaaatcct accatgtgct    960
aagttatcat actgaacact agaaaatatt aataatagtt acaaataata gcattttgga   1020
tacatgtata tgcatggctg aatcccttg ctgttcactt gaaactacca caacattgtt   1080
aatcaaatat atcccaatac aaaataaatt ttaaagtttg aaaaaaataa taacattctg   1140
ctaaactagt atggatgagt atgtgtgggt tctgtatata gacatacatt atttcttgaa   1200
tatagatcga taggtaatgt agtattctgt ttttcctttc aggttggact ggaaaatcta   1260
tcttctacag tttcatatct accactttac ttcatacaac cagcatgttt ggagtggtgc   1320
atcaataaga caaatcgcag agtatttcct gaattattta tactctcyct gttagtttat   1380
attgaatata ctgggtttat atggtggttt catacaaact tagctgatga ttatttaaaa   1440
tcctttccct actcttctg agttatagaa atattttct ttccctctga gaataaaatt   1500
tcaagtgaat tcctgcagcc cggggatcca ctagttctag agcg                   1544
```